US 6,635,021 B1

(12) United States Patent
Sullivan et al.

(10) Patent No.: US 6,635,021 B1
(45) Date of Patent: *Oct. 21, 2003

(54) METHOD AND APPARATUS USEFUL IN THE DIAGNOSIS OF OBSTRUCTIVE SLEEP APNEA OF A PATIENT

(75) Inventors: Colin Edward Sullivan, Sydney (AU); Christopher Lynch, North Ryde (AU)

(73) Assignee: ResMed Limited, North Ryde (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/934,176

(22) Filed: Sep. 19, 1997

Related U.S. Application Data

(63) Continuation of application No. 08/838,462, filed on Apr. 7, 1997, now abandoned, which is a continuation of application No. 08/654,742, filed on May 29, 1996, now abandoned, which is a continuation of application No. 08/385,742, filed on Feb. 8, 1995, now abandoned, which is a division of application No. 08/100,556, filed on Jul. 30, 1993, now abandoned, which is a division of application No. 07/892,692, filed on May 27, 1992, now Pat. No. 5,245,995, which is a continuation of application No. 07/548,108, filed on Jul. 5, 1990, now abandoned, which is a continuation-in-part of application No. 07/457,757, filed as application No. PCT/AU88/00215 on Jun. 27, 1988.

(30) Foreign Application Priority Data

Sep. 8, 1987 (AU) .............................................. PI 4234
Jun. 26, 1997 (AU) .............................................. PI 2730

(51) Int. Cl.⁷ ................................................. A61B 5/08
(52) U.S. Cl. .................. 600/529; 600/538; 128/204.23; 128/205.25; 128/207.13
(58) Field of Search ....................... 128/204.18, 204.21, 128/204.23, 207.13, 207.14, 207.18, 205.23, 205.25; 600/483, 484, 529, 532, 586, 533, 538

(56) References Cited

U.S. PATENT DOCUMENTS

| 2,904,033 A | 9/1959 | Shane |
| 3,559,638 A | 2/1971 | Potter |
| 3,595,228 A | 7/1971 | Simon et al. |

(List continued on next page.)

FOREIGN PATENT DOCUMENTS

| DE | 3015279 A1 | 10/1981 |
| DE | 3345067 A1 | 6/1984 |
| DE | 3429345 A1 | 6/1985 |

(List continued on next page.)

OTHER PUBLICATIONS

Healthdyne Technologies Product brochure for "Tranquility Plus," undated.
DeVilbiss Health Care, Inc. product brochure for "Revitalizer Soft–Start," 1991.
Healthdyne Technology magazine advertisement for "Tranquillty Plus," Nov. 1990.

(List continued on next page.)

*Primary Examiner*—R S Smith
(74) *Attorney, Agent, or Firm*—Pillsbury Winthrop LLP

(57) ABSTRACT

Patients may operate a CPAP system to deliver appropriate airway pressure at their home. A patient's apnea problem can be diagnosed at home without supervision with a CPAP device which delivers a continuously minimum appropriate pressure for substantially the entire period of therapy.

138 Claims, 10 Drawing Sheets

U.S. PATENT DOCUMENTS

| | | | |
|---|---|---|---|
| 3,611,801 A | 10/1971 | Paine et al. | |
| 3,802,417 A | 4/1974 | Lang | |
| 3,817,246 A | 6/1974 | Weigl | |
| 3,834,383 A | 9/1974 | Weigl et al. | |
| 3,840,006 A | 10/1974 | Buck et al. | |
| 3,863,630 A | 2/1975 | Cavallo | |
| 3,882,847 A | 5/1975 | Jacobs | |
| 3,903,875 A | 9/1975 | Hughes | |
| 3,914,994 A | 10/1975 | Banner | |
| 3,926,177 A * | 12/1975 | Hardway, Jr. et al. | 340/279 |
| 3,932,054 A | 1/1976 | McKelvey | |
| 3,961,627 A | 6/1976 | Ernst et al. | |
| 3,972,327 A | 8/1976 | Ernst et al. | |
| 3,985,467 A | 10/1976 | Lefferson | |
| 3,989,037 A | 11/1976 | Franetzki | |
| 4,006,634 A | 2/1977 | Billette et al. | |
| 4,016,876 A * | 4/1977 | Martin et al. | 128/202 |
| 4,083,245 A | 4/1978 | Osborn | |
| 4,239,039 A | 12/1980 | Thompson | |
| 4,312,235 A | 1/1982 | Daigle | |
| 4,322,594 A | 3/1982 | Brisson | |
| 4,347,468 A | 8/1982 | Wilke | |
| 4,381,788 A | 5/1983 | Douglas | |
| 4,387,722 A | 6/1983 | Kearns | |
| 4,414,982 A | 11/1983 | Durkan | |
| 4,430,995 A | 2/1984 | Hilton | |
| 4,433,693 A | 2/1984 | Hochstein | |
| 4,448,058 A | 5/1984 | Jaffe et al. | |
| 4,452,252 A * | 6/1984 | Sackner | 600/529 |
| 4,499,914 A | 2/1985 | Schebler | |
| 4,537,190 A | 8/1985 | Caillot et al. | |
| 4,550,615 A | 11/1985 | Grant | |
| 4,550,726 A | 11/1985 | McEwen | |
| 4,558,710 A | 12/1985 | Eichler | |
| 4,570,631 A | 2/1986 | Durkan | |
| 4,580,575 A | 4/1986 | Birnbaum et al. | |
| 4,595,016 A | 6/1986 | Fertig et al. | |
| 4,602,644 A * | 7/1986 | DiBenedetto et al. | 128/207.18 |
| 4,619,270 A * | 10/1986 | Margolis et al. | 128/721 |
| 4,630,614 A | 12/1986 | Atlas | |
| 4,637,386 A | 1/1987 | Baum | |
| 4,648,396 A | 3/1987 | Raemer | |
| 4,648,407 A | 3/1987 | Sackner | |
| 4,677,975 A | 7/1987 | Edgar et al. | |
| 4,686,974 A | 8/1987 | Sato et al. | |
| 4,686,999 A * | 8/1987 | Snyder et al. | 128/716 |
| 4,738,266 A | 4/1988 | Thatcher | |
| 4,777,963 A | 10/1988 | McKenna | |
| 4,782,832 A | 11/1988 | Trimble et al. | |
| 4,795,314 A | 1/1989 | Prybella et al. | |
| 4,802,485 A | 2/1989 | Bowers et al. | |
| 4,803,471 A | 2/1989 | Rowland | |
| 4,819,629 A | 4/1989 | Jonson | |
| 4,823,788 A | 4/1989 | Smith et al. | |
| 4,825,802 A | 5/1989 | Le Bec | |
| 4,827,922 A | 5/1989 | Champain et al. | |
| 4,838,257 A | 6/1989 | Hatch | |
| 4,838,258 A | 6/1989 | Dryden et al. | |
| 4,838,275 A * | 6/1989 | Lee | 128/904 |
| 4,844,085 A | 7/1989 | Gattinoni | |
| 4,860,766 A | 8/1989 | Sackner | |
| 4,870,960 A | 10/1989 | Hradek | |
| 4,915,103 A | 4/1990 | Visveshwara et al. | |
| 4,938,210 A | 7/1990 | Shene | |
| 4,938,212 A | 7/1990 | Snook et al. | |
| 4,957,107 A | 9/1990 | Sipin | |
| 4,960,118 A | 10/1990 | Pennock | |
| 4,971,065 A | 11/1990 | Pearce | |
| 4,972,842 A | 11/1990 | Korten et al. | |
| 4,982,738 A * | 1/1991 | Griebel | 600/483 |
| 4,986,269 A | 1/1991 | Hakkinen | |
| 5,024,219 A | 6/1991 | Dietz | |
| 5,052,400 A | 10/1991 | Dietz | |
| 5,063,922 A | 11/1991 | Hakkinen | |
| 5,105,354 A | 4/1992 | Nishimura | |
| 5,117,819 A | 6/1992 | Servidio et al. | |
| 5,134,995 A * | 8/1992 | Gruenke et al. | 128/204.23 |
| 5,170,798 A | 12/1992 | Riker | |
| 5,195,528 A | 3/1993 | Hok | |
| 5,199,424 A | 4/1993 | Sullivan et al. | |
| 5,231,983 A | 8/1993 | Matson et al. | |
| 5,239,995 A | 8/1993 | Estes et al. | |
| 5,245,995 A * | 9/1993 | Sullivan et al. | 128/204.23 |
| 5,259,373 A | 11/1993 | Gruenke et al. | |
| 5,313,937 A | 5/1994 | Zdrojkowski | |
| 5,322,057 A | 6/1994 | Raabe et al. | |
| 5,388,571 A | 2/1995 | Roberts et al. | |
| 5,433,193 A | 7/1995 | Sanders et al. | |
| RE35,295 E | 7/1996 | Estes et al. | |
| 5,549,106 A | 8/1996 | Gruenke et al. | |
| 5,660,171 A | 8/1997 | Kimm et al. | |
| 5,845,636 A | 12/1998 | Gruenke et al. | |

FOREIGN PATENT DOCUMENTS

| | | |
|---|---|---|
| DE | 3537507 A1 | 4/1987 |
| EP | 0 066 451 A1 | 12/1982 |
| EP | 0 164 500 A2 | 3/1985 |
| EP | 171321 | 2/1986 |
| EP | 0 171 321 A1 | 2/1986 |
| EP | 0 236 850 A2 | 9/1987 |
| EP | 298 367 A2 | 1/1989 |
| EP | 0 425 092 A1 | 9/1989 |
| EP | 0 452 001 A2 | 3/1990 |
| GB | 1432572 | 4/1976 |
| GB | 1583273 | 1/1981 |
| GB | 2 077 444 A | 12/1981 |
| GB | 2 164 569 A | 3/1986 |
| GB | 2 166 871 A | 5/1986 |
| GB | 2 221 302 A | 1/1990 |
| JP | 54-104369 | 8/1979 |
| JP | 62-103297 | 4/1987 |
| JP | 63-275352 | 11/1988 |
| SU | 238077 | 7/1969 |
| WO | WO 82/03326 | 10/1982 |
| WO | 82/03548 | 10/1982 |
| WO | 86/05965 | 10/1986 |
| WO | WO 86/06969 | 12/1986 |
| WO | 87/02677 | 5/1987 |
| WO | WO 88/10108 | 12/1988 |
| WO | WO 90/14121 | 1/1990 |

OTHER PUBLICATIONS

Puritan Bennett's product brochure for "Companion 318" undated.
Sefam's product brochure for "REM Plus," undated.
Medical Industries America Inc.'s product brochure for "Sleepap," undated.
Lifecare's product brochure for "CPAP–100" Jul. 1991.
ResCare, Ltd.'s product brochure for "Sullivan CPAP APD 2" undated.
Respironics, Inc.'s product brochure for "REMstar Choice Nasal CPAP System," dated 1991.
"The Role of Press Support . . . " Kacmarek R.M. Respiratory Care, Feb. 1988 vol 33m No 2 pp 99–120.
"Response Time: Flow by vs. Pressure", Dupuls, U.G. RRT Vol 24, iss, Mar. 3, 1988, pp 5–6.
"Flowby–Opinion 50" Puritan–Bennett Corp., pub # 20535A, Oct. 1986, pp 1–6, Overland Park, KS, USA & Pub # AA–1144 Jan. 1987.

"Investigation of the Spontaneous . . . ", Cox et al. Intensive Care Med., 1988 14:532–537.

Ancoli–Israel et al., "Comparisons of home sleep recordings and polysomnograms in older adults with sleep disorders", Sleep, 1981, 4(3):283–291.

Gyulay et al., Evaluation of a microprocessor–based portable home monitoring system to measure breathing during sleep, Sleep, 1987, 10(2):130–142.

Cummisky et al., "The detection and quantification of sleep apnea by tracheal sound recordings", Am Rev Respir Dis, 1982; 126:221–224.

J. Peirick et al., "Automated apnoea detection by computer: analysis of tracheal breath sounds", Medical & Biological Engineering & Computing, Sep. 1983, pp 632–635.

* cited by examiner

A = AVERAGE OF THE LAST 64 INHALES
B = AVERAGE OF THE LAST 4 INHALES
IF $B < \frac{A}{X}$ THEN OBSTRUCTION IS DEVELOPING.
X = SET LIMIT FOR OBSTRUCTION DETECTION.

METHOD AND APPARATUS USEFUL IN THE DIAGNOSIS OF OBSTRUCTIVE SLEEP APNEA OF A PATIENT

CROSS REFERENCE TO RELATED APPLICATIONS

This application is a continuation of U.S. application Ser. No. 08/838,462, filed Apr. 7 1997, now abandoned, which is a continuation of U.S. application Ser. No. 08/654,742, filed May 29, 1996, now abandoned, which is a continuation of U.S. application Ser. No. 08/385,742, filed Feb. 8, 1995, now abandoned, which is a divisional of U.S. application Ser. No. 08/100,556, filed Jul. 30, 1993, now abandoned, which is a divisional of U.S. application Ser. No. 07/892,692, filed May 27, 1992, now U.S. Pat. No 5,245,995, which is a continuation of U.S. application Ser. No. 07/548,108, filed Jul. 5, 1990, now abandoned, which is a continuation-in-part of U.S. application Ser. No. 07/1457,757, filed Dec. 21, 1989, filed as PCT AU88/00215 on Jun. 27, 1988, published as WO 88/10108 on Dec. 29, 1998, now abandoned, all of which hereby incorporated by reference in their entirety.

BACKGROUND ART

The present invention relates to the diagnosis and treatment of partial or complete upper airway occlusion, a condition where the upper airway collapses, particularly under the reduced pressure generated by inhalation. This is most likely to happen during unconsciousness, sleep or anaesthesia.

A particular application of the present invention is to the diagnosis and/or treatment of snoring and sleep apnea. Sleep apnea is characterized by complete occlusion of the upper airway passage during sleep while snoring is characterized by partial occlusion. Obstructive sleep apnea sufferers repeatedly choke on their tongue and soft palate throughout an entire sleep period resulting in lowered arterial blood oxygen levels and poor quality of sleep. It should be realized that although the following specification discusses sleep apnea in detail, the present invention also applies to the diagnosis and treatment of other forms of upper airway disorders.

Reference to international patent publication WO 82/03548 will show that the application of continuous positive airway pressure (CPAP) has been used as a means of treating the occurrence of obstructive sleep apnea. The patient is connected to a positive pressure air supply by means of a nose mask or nasal prongs. The air supply breathed by the patient, is at all times, at slightly greater than atmospheric pressure. For example, gauge pressures will typically be within the range of 2 cm to 25 cm. It has been found that the application of continuous positive airway pressure provides what can be described as a "pneumatic splint", supporting and stabilizing the upper airway and thus eliminating the occurrence of upper airway occlusions. It is effective in eliminating both snoring and obstructive sleep apnea and in many cases, is effective in treating central and mixed apnea.

The airway pressure required for effective CPAP therapy differs from patient to patient. In order to discover the airway pressure which is most effective for a particular individual, the practice has been for the patient to undergo two sleep studies at an appropriate observation facility such as a hospital, clinic or laboratory. The first night is spent observing the patient in sleep and recording selected parameters such as oxygen saturation, chest wall and abdominal movement, air flow, expired $CO_2$, ECG, EEG, EMG and eye movement. This information can be interpreted to diagnose the nature of the sleeping disorder and confirm the presence or absence of apnea and where present, the frequency and duration of apneic episodes and extent and duration of associated oxygen desaturation. Apneas can be identified as obstructive, central or mixed. The second night is spent with the patient undergoing nasal CPAP therapy. When apnea is observed the CPAP setting is increased to prevent the apnea. The pressure setting at the end of the sleep period, i.e., the maximum used, is deemed to be the appropriate setting for that patient. For a given patient in a given physical condition there will be found different minimum pressures for various stages of sleep in order to prevent occlusions. Furthermore, these various pressures will, in fact, vary from day to day depending upon the patient's physical condition, for example, nasal congestion, general tiredness, effects of drugs such as alcohol, as well as their sleeping posture. Thus the appropriate pressure found in the laboratory is necessarily the maximum of all -these minimum pressures for that particular night and is not necessarily the ideal pressure for all occasions nor for every night. It will generally be higher than necessary for most of the night.

Also patients must be able to operate a CPAP system to deliver appropriate airway pressure at their home where their general physical condition or state of health may be quite different to that in the sleep clinic, and will certainly vary from day to day. The patient's physical condition often improves due to CPAP therapy. It is often the case that after a period of therapy the necessary airway pressure can be reduced by some amount while still preventing the occurrence of obstructive sleep apnea. However, the prior art provides no facility to take advantage of this fact other than by regular diagnostic sleep periods in a sleep clinic or hospital.

The long term effects of CPAP therapy are unknown so it is desirable to keep the airway pressure as low as practicable, particularly if a patient requires long term treatment. Lower airway pressures also result in a lower face mask pressure which is generally more comfortable for the patient. It has been found that CPAP induces patients to swallow and this inducement to swallow can be reduced by lowering the airway pressure. Thus it is desirable to use the lowest practicable airway pressure that is effective in preventing airway occlusion during CPAP therapy for the comfort and, possibly, the long term safety of the patient. Also, a lower airway pressure requires less energy consumption and a less complex and therefore less expensive apparatus which is generally quieter.

Low airway pressures are also desirable before and during the early stage of each sleep period as the increased comfort of an initially lower airway pressure allows the patient to more easily fall asleep. When a patient undergoing CPAP opens his mouth with pressurized air being forced through the nose the pressured air exits out of the mouth producing an unpleasant sensation. This can occur when the patient puts on the mask connected to the pressured air supply before falling asleep and some patients will therefore leave the mask off for as long as possible and may in fact fall asleep without wearing the mask and therefore without the benefits of the CPAP therapy.

Presently available CPAP units do hot address this problem and so there is a need to provide a CPAP device which will be more acceptable to the patient before and during initial sleep by operating at an initially low pressure but automatically increasing to an appropriate therapeutic pressure before apnea occurs.

In addition to the problems associated with administering CPAP therapy there exists the inconvenience and cost of diagnosis which is currently undertaken by overnight observation at a sleep clinic or the like. Hence a simple means whereby a patient's apnea problem can be diagnosed at home without supervision is clearly desirable as well as a CPAP device which will deliver a continuously minimum appropriate pressure for substantially the entire period of therapy.

Devices are available to detect apnea. For example, International Patent publication WO/86/05965 discloses an apparatus which includes acoustic respiration sensors, background sound sensors and movement sensors. Such apparatus are capable of detecting breathing sounds, comparing those sounds with body movements and background noises and by further comparing the results with a data base of information, to indicate whether the patient is undergoing a normal or abnormal breathing pattern. Such apparatus can sound an alarm on the occurrence of apnea.

Another device which could be readily adapted to detect and record the occurrence of apneic episodes is disclosed in U.S. Pat. No. 4,537,190. That apparatus is responsive to the $CO_2$ levels in exhaled air during respiration and is also responsive to the absence of respiration (i.e., apnea) in which case it can switch on a ventilator.

These devices are deficient in that they do not take advantage of the indication of apnea obtained exclusively from a recording from a single sound transducer (microphone) preferably located in the CPAP nose mask or prongs that can be interpreted by a skilled physician. The sound transducer, in its most general form, consists of a pressure transducer which, in addition to detecting snoring sounds, can detect other respiratory parameters such as the rate of breathing, inhaled air flow or inhaled air flow rate. The inherent simplicity of this form of measurement makes it safe and practicable for anybody to use in their own home with a minimum of prior instruction.

Although diagnosis in a sleep clinic as outlined above is beneficial, it has some deficiencies. A patient is likely not to sleep in a fully relaxed state in an unfamiliar environment and a single night is insufficient to obtain a pressure setting that will be optimal in the long run. Thus home therapy at the pressure setting arrived at in this way is likely to be less than 100% effective on some occasions and higher than necessary for a substantial portion of the time. The cost and inconvenience of a sleep study in a hospital setting are to be avoided if possible.

A skilled physician can usually recognize the symptoms of sleep apnea from questioning and examining a patient. Where no other indications are present there is very little risk in attempting nasal CPAP therapy without further testing as the treatment is fail safe and non-invasive. However, a very useful intermediate step would be to analyze the pattern of respiratory sounds over one or more full nights of sleep. Interpretation of these patterns together with questioning and examination will, in many cases, provide sufficient confirmation of apnea to prescribe nasal CPAP therapy. If nasal CPAP eliminates the symptoms of day time sleepiness (as assessed by the patient) and of apneic snoring patterns (as assessed by analysis of recorded respiratory sounds while on nasal CPAP), the treatment can be continued. Further check ups can be conducted at intervals recommended by the physician.

In the most general form of the device, the intermediate step before attempting nasal CPAP therapy would be to analyse the patterns of the respiratory parameters that can be obtained from a single pressure transducer. These parameters include, in addition to acoustic rate of breathing, inhaled/exhaled air volume and inhaled/exhaled air flow rate, and provide comprehensive information for the physician to assess the patient's condition. This additional information, coming from the same pressure transducer, is available at marginal additional cost to the acoustic recording and with no additional complexity in home use by the patient.

The measurement of other parameters would provide further information to assist diagnoses and the acoustic and/or other respiratory recordings described above can readily be used in conjunction with other monitors such as ECG and/or pulse oximetry. Suitable monitors are available to measure both these parameters in the home but with increased information comes much higher cost of equipment and increase complexity in using the equipment. The correlation between reduced oxygen saturation and apnea is sufficiently well established to infer oxygen desaturation from the confirmation of an apneic event.

Diagnoses which are not conclusive from examination and home monitoring will continue to be confirmed from full sleep studies in a Sleep Disorders Center.

Thus the prior art monitors and methods are deficient at least in that the resulting therapy is not 100% effective at all times, it is delivered at higher pressure than necessary for substantial periods, the equipment is expensive and has required diagnosis in specialized clinics.

DISCLOSURE OF INVENTION

The present inventors have recognized the detection of the noise of snoring or more particularly snoring patterns as a reliable parameter for detecting apneas as well as the imminent onset of apneic episodes. Characteristic snoring patterns can be associated with various sleep conditions including apnea and in fact in most (perhaps 95%) of sleep apnea sufferers, distinctive snoring patterns closely precede apneic episodes as will be later discussed. Characteristic patterns of other respiratory parameters such as rate of breathing, inhaled/exhaled air volume and inhaled/exhaled air flow rate, obtainable from the same pressure transducer as snoring patterns, can also be used for detecting apneas as well as the imminent onset of apneic episodes. Any one parameter or combination of parameters may be used for detecting apneas or other breathing disorders, as well as the imminent onset of apneas or other breathing disorders.

A pressure transducer such as a microphone is a suitable detector of these characteristic snoring sounds, and in particular the sounds of snoring patterns. Furthermore, the quality of the sounds monitored can be enhanced by placing the microphone within an enclosure which is in sound communication with a patient's respiratory system. By enclosing the microphone, a physical noise barrier isolates the microphone from external sounds. If the enclosure is in sound communication with the patient's respiratory system the natural stethoscope effect of the patient's respiratory system is thereby exploited. A further benefit of such a device is that the microphone is not in direct contact with any part of the patient's body. Thus, relative movement between the microphone and the patient's body, which is a noise source as far as monitoring is concerned, can be avoided.

Monitoring of a patient's snoring patterns alone can in many instances provide information indicative of his/her condition, whether he/she suffers mild, medium or extreme apneic episodes, how often the episodes occur and therefore whether CPAP therapy will be beneficial. A snoring monitor can accordingly be used at least as a preliminary diagnostic tool with or without monitoring other physiological parameters to provide information on the frequency and severity of snoring, hypopnea and apnea in a patient. Its simplicity and inexpensive nature allows it to be used at home in the patient's usual environment without the expense of a night in a sleep clinic. In some cases, e.g., where unusual snoring patterns are encountered, the diagnosis of the data from the snoring monitor will not be conclusive and the traditional full diagnosis in a sleep clinic will be required.

Thus, in one form of this invention there is provided a diagnostic device comprising a nose piece substantially fluidly sealable to the nasal air passages of a patient, a sound transducer in sound communication with the interior of the nose piece so as to be, when in use, in sound communication with the respiratory system of the patient and to detect and produce a signal responsive to the sounds of patient snoring, and recording equipment associated with the sound transducer for recording information indicative of the signal.

In another form of the diagnostic device, there is provided a nose piece substantially fluidly sealable to, or in sealed fluid communication with, the nasal air passages of a patient, a pressure transducer in pressure communication with the interior of the nose piece so as to be in pressure communication with the respiratory system of the patient and to detect and produce a signal or signals responsive to snoring and other respiratory parameters, such as rate of breathing, inhaled/exhaled air volume and inhaled/exhaled air flow rate, of the patient, and recording equipment associated with the pressure transducer for recording information indicative of one or more of the signals.

In one preferred embodiment of the diagnostic device, the intensity of the signal is recorded with respect to time. In another embodiment of the diagnostic device the microphone output is fed through an amplifier or filter to differentiate normal breathing sounds from those indicative of snoring, and the intensities and time pattern of the differentiated sounds are recorded. Further, in a embodiment of the diagnostic device the frequency and duration of airway occlusions are calculated by preprogrammed processing of the detected signal, the processed signal is recorded as a time chart or a table interpreted by the physician.

In another embodiment of the diagnostic device, the pressure transducer measures or detects a number of audio or low frequency waves generated within the mask during breathing including a high frequency audio wave produced by the air flow into the mask and by the rotating elements of the air source, a low frequency audio wave produced by the resonance of the airways or chest cavity during snoring, a very low frequency large amplitude wave corresponding to the pressure variations produced by the air flowing over a section of the nose piece, which may include a flow restrictor to amplify the pressure drop. After suitable amplification, the output signal from the pressure transducer passes through filtering and conditioning circuits to separate the different waves of interest, including the low frequency audio wave described above and the very low frequency pressure wave produced by the air flowing over the said section of the nose piece.

The breathing rate or interruption of breathing, the air flow rate during inhalation/exhalation and the beginning/end points of the breathing cycle are derived from the very low frequency pressure wave after further. sampling or processing. Using a suitable integration technique, the air flow is integrated for the duration of the inspiration and/or expiration phase using the said beginning/end points. This integral of air flow corresponds to the inhaled/exhaled air volume for each breath. The processed signals are recorded as a time chart or a table interpreted by a physician.

Thus in a number of cases such a snoring monitor provides an effective substitute for the traditional first night in the sleep clinic. The monitor in its more general form provides information on respiratory parameters such as rate of breathing, inhaled/exhaled air volume, and inhaled/exhaled air flow rate, as well as snoring. Where diagnosis indicates CPAP therapy to be appropriate the patient can go straight to the traditional second night at the sleep clinic so as to determine their appropriate CPAP setting for their condition, or they could commence use of an automatic CPAP device such as the unit described hereunder.

The monitoring of snoring patterns is useful not only for recording information regarding those patterns for diagnostic purposes but is also useful in that certain snoring patterns are a precursor to most apneic episodes in a large proportion of sleep apnea victims. Thus, an effective CPAP device can be controlled by a feedback system in which snoring patterns are monitored and CPAP pressure is raised at the detection of predefined snoring patterns so as to provide increased airway pressure before, and in fact generally prevent the occurrence of, apneic episodes.

Thus, in another form of the invention there is provided in a CPAP apparatus a feedback control comprising a sound monitoring device in sound communication with the respiratory system of a patient when using the apparatus, and a processor responsive to output from the sound monitoring device so as to control CPAP pressure according to patient requirements as determined by output from the sound monitoring device in order to prevent apneic episodes.

The monitoring of other respiratory parameters, as well as snoring, is also useful not only for recording those patterns for diagnostic purposes but is also useful in that certain patterns of these parameters are a precursor to most apneic episodes and other forms of breathing disorders that can be treated by nasal CPAP. Thus an effective CPAP device can be controlled by a feedback system in which patterns of respiratory parameters are monitored and CPAP pressure is raised at the detection of pre-defined patterns so as to provide increased airway pressure, before and in fact generally prevent the occurrence of apneic episodes or other forms of breathing disorders.

For example, the air flow rate inhaled or exhaled by the patient is compared to a base line level for that patient and if the flow rate is lower than the base line, the CPAP pressure is raised. Alternatively, the time interval between the onset of each inspiration or expiration is compared to a base line level for that patient and if the interval is greater than the base line, the CPAP pressure is raised. Alternatively, the integrated inhaled or exhaled volume of air is averaged over a relatively large number of breaths to give a moving base line for the patient. Simultaneously, the integrated inhaled or exhaled volume of air is averaged over a short time interval. If the volume over the short time interval is less than the volume over the relatively large number of breaths by a specified amount, CPAP pressure is raised.

Preferably, the feedback control is co-operative with a variable speed air compressor of the CPAP apparatus, the processor regulating the speed of the compressor when in use by increasing speed in response to a said signal equivalent to a preprogrammed signal indicative of a predetermined snoring pattern. The said signal could also be indicative of a predetermined pattern in other respiratory parameters.

Preferably, the control system furthermore decreases speed of the air compressor in the absence of the signal after a period of time in accordance with the predefined procedure.

In another form of the feedback device of the invention there is provided a CPAP apparatus including a variable speed air compressor, a nose piece for sealed air communication with a patient's respiratory system, an air line from the compressor to the nose piece, an enclosed microphone connected to the air line so as to be in sound communication with the patient's respiratory system, and a feedback system controlling the speed of the air compressor in response to an output from the microphone so as to increase compressor speed in response to detected sound indicative of heavy snoring in accordance with a pre-defined procedure. Preferably, the feedback system reduces the speed of the air compressor in response to an absence of the said sound in accordance with the predefined procedure.

In another form of the apparatus there is provided a CPAP apparatus including a variable speed air compressor, a nose piece for sealed air communication with a patient's respiratory system, an air line from the compressor to the nose piece, a pressure transducer connected to the air line so as to be in pressure communication with the patient's respiratory system, and a feedback system controlling the speed of the air compressor in response to an output or outputs from the pressure transducer so as to increase compressor speed in response to detected patterns of sound or respiratory parameters indicative of snoring or breathing disorders in accordance with a predefined procedure. Preferably the feedback system reduces the speed of the air compressor in response to an absence of the said patterns of sound or respiratory parameters in accordance with the predefined procedures.

Disadvantages in the prior art are also ameliorated by a further aspect of the invention which provides a variable speed air compressor and control system in the CPAP apparatus, the control system regulating the speed of the compressor when in use by increasing its speed in accordance with a predefined procedure whereby the commencement of operation of the compressor occurs at a preselected minimum speed with a gradually increasing compressor speed over a preselected period of time to a preselected maximum speed.

This embodiment of the invention provides an advantage in that the patient is exposed to a comfortably low pressure before falling asleep and during initial stages of sleep while the necessary therapeutic pressure is reached by the time it is required.

BRIEF DESCRIPTION OF THE DRAWINGS

The present invention will now be described in detail by way of reference to the attached drawings in which.

BEST MODE OF CARRYING OUT THE INVENTION

Figures 1A, 1B:
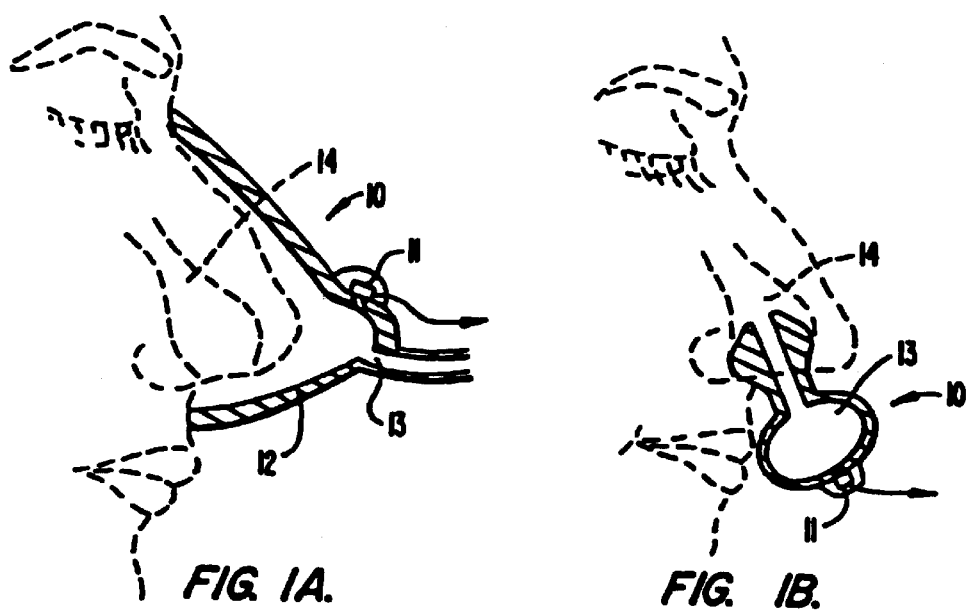
FIG. 1a is a schematic sectional view of one embodiment of a snoring detection apparatus in accordance with the present invention.
FIG. 1b is a schematic sectional view of another embodiment of a snoring detection apparatus in accordance with the present invention.

FIG. 1a illustrates a snoring detection device 10 comprising a microphone 11, in sound communication with the container 12 of a nose mask. Air, being inhaled by the patient, enters the nasal passageways 14 through the opening 13 in the nose mask 12 and is exhaled in the reverse direction. As the airway extends from the source of snoring sounds within the patient's body, through the nasal passages 14 and out of the opening 13 in the nasal mask, the microphone 11 is ideally located to take advantage of the natural stethoscope formed by the enclosed airway. Hence the snoring and breathing sounds are focused and concentrated by this arrangement. Alternatively, the microphone 11 may be located within, or attached externally of, a nasal prong device as illustrated in FIG. 1b. The detection device 10 can be used in a diagnostic device or a feedback control. In the case of the detection device 10 being used in diagnostic equipment there is connected to the microphone 11 an electronic processor/recorder which records signals from the microphone 11 either on a time basis or after preprogrammed processing so as to record for example tables of indexes such as the number of apneic episodes, their duration, etc. The recorded data can then be reviewed by the physician for diagnosis.

Figure 2A:
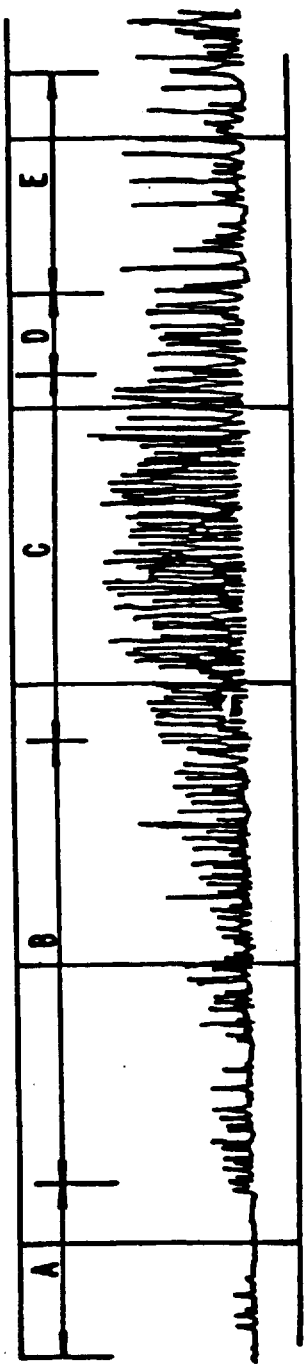
FIG. 2a is a slow recording of sound levels obtained using the monitor of the present invention for a patient suffering from sleep apnea.

FIG. 2a shows a graph representing sound amplitudes recorded from the snoring detection device 10. The major calibration in the time scale direction represents two minutes.

The effect of blower motor noise can be diminished or completely removed by setting a low gain on the recording device or passing the signal through an amplitude filter to effectively ignore all sounds below a particular minimum amplitude or by passing the signals through a low pass frequency filter to effectively ignore sounds above its cut-off frequency. An alternative method is to use a sound attenuator in the air line proximate the blower.

Part A of FIG. 2a is indicative of normal breathing, part B indicates soft to moderate snoring, part C shows constant loud snoring and part E shows periods of silence punctuated by snoring. In section D of the chart of FIG. 2a, it can be seen that the breathing sound intensity rises and falls. This is indicative of obstructive hypopnea, a condition in which the breath-by-breath intensity decreases progressively, and then increases. In this pattern the decreasing intensity of the snoring occurs when the upper airway is almost, but not entirely, sucked closed by strong inspiratory efforts. This pattern is a "pre-apneic" pattern.

The following part E, is therefore quickly interpreted by a skilled physician as being indicative of sleep apnea, with periods of airway occlusion which terminate with one or more loud breathing sounds followed by further occlusions.

Figure 2B:
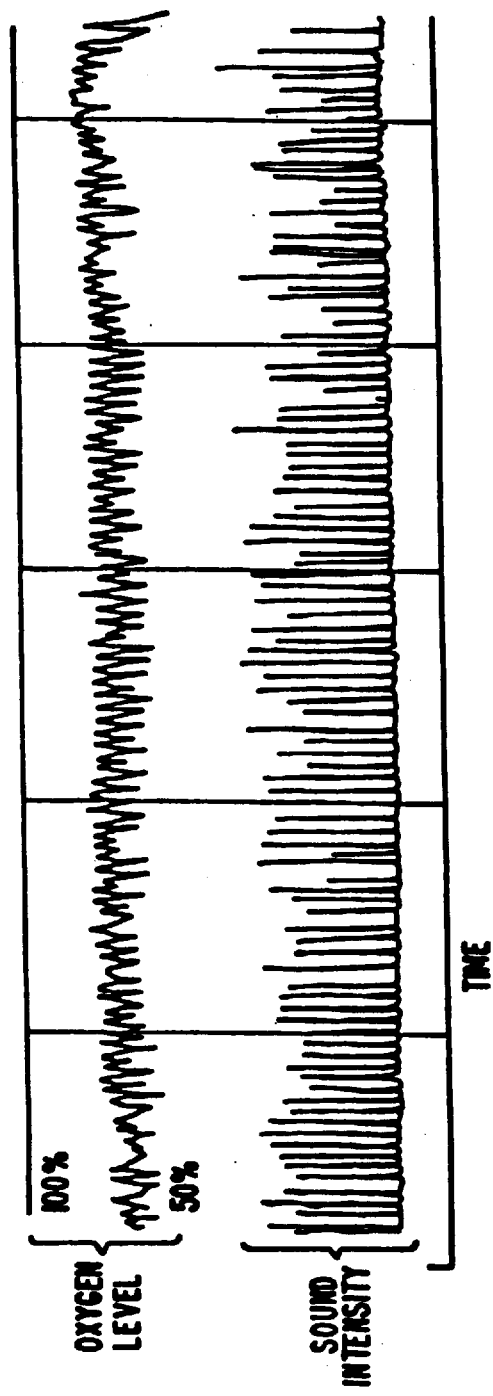
FIG. 2b shows the correlation of sound patterns and blood oxygen levels during a period of repetitive obstructive apnea.

The correlation between snoring patterns and arterial oxygen is shown in FIG. 2b. Clearly the snoring patterns are an accurate parameter for detecting imminent apneic episodes, and more importantly periods of low oxygen supply to the brain and other organs.

Thus recorded information derived from the signal of the device 10 can be used for diagnostic purposes, such as initial diagnosis of sleep apnea, without the need for the patient to stay overnight at an observation facility. The sound patterns can be analyzed by a programmed microprocessor within the diagnostic unit so as to record tables of indexes such as number of apneic episodes, their duration and time of occurrence. This is of economic significance because the cost of one overnight observation is comparable to the purchase price of a CPAP device.

The nose prongs and mask 12 are convenient forms of containers for the monitor device 10 however the container could take any other convenient form.

Furthermore, diagnostic apparatus in accordance with the present invention is suited for use by a patient with minimal supervision and therefore may be used successfully at home, the recorded diagnostic information being conveniently presented for expert analysis.

Figure 3:
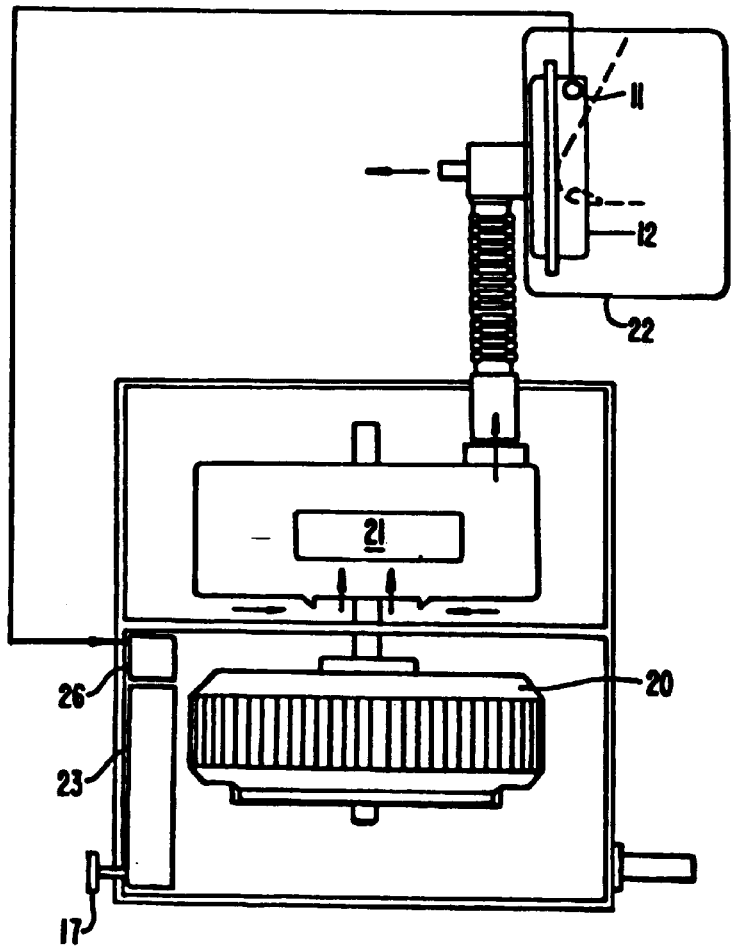
FIG. 3 is a diagram of a further embodiment of the present invention.

In FIG. 3, a CPAP apparatus embodying the invention is illustrated. The CPAP unit comprises a motor 20 which drives a blower 21. The speed of the motor 20 is controlled by an electronic speed control unit 23. As an increase in motor speed also increases the blower speed which in turn increases the output air pressure of the blower 21, the speed control unit can be manipulated to vary the output pressure of the blower 21. The CPAP device also includes a snoring detection means 22 wherein sounds are detected by a microphone 11. In its most general form, the snoring detection means 22 is a pressure detection means and microphone 11 is a differential pressure sensor. The snoring detection means 22 is conveniently in the form of the previously described device 10. Electrical impulses are fed from said microphone 11 to an amplifier/filter/processor unit 26 which generates an electrical signal when snoring sounds occur. The motor speed control means is electrically connected to the snoring detection device 22 and increases the speed of the electric motor 20 by an analogue means in response to the electrical signal generated by the snoring detection device. Accordingly, the output pressure of the CPAP unit increases in response to detection of snoring.

When a snore or sequence of snores is detected by the snoring detection means 22 a signal is generated. The speed control unit 23 increases the speed of the fan motor and the output pressure is increased. As snoring is caused by vibration of the soft palate, it is therefore indicative of an unstable airway and, as previously described, is a warning signal of the imminence of upper airway occlusion in patients that suffer obstructive sleep apnea. Snoring is itself undesirable not only as it is a disturbance to others but it is strongly believed to be connected with hypertension. If the resultant increase in CPAP pressure is sufficient to completely stabilize the airway, snoring will cease. If a further snoring sound is detected, the CPAP pressure is increased again. This process is repeated until the upper airway is stabilized and snoring ceases. Hence, the occurrence of obstructive apnea can be eliminated by application of a minimum appropriate pressure at the time of use.

In order to ensure that the CPAP pressure is maintained at a level as low as practicable to prevent the onset of apnea, the preferred embodiment also includes a means to decrease the pressure if an extended period of snore free breathing occurs. For example, this can be done by automatically reducing the CPAP pressure at a gradual rate as long as snoring is not detected. The rate at which the CPAP pressure is decreased in the absence of snoring is preferably much less than the rate at which it is increased when snoring is detected. This can be achieved, for example, by the amplifier/filter/processor unit 26, in the absence of an electronic signal from the microphone 11, continuously gradually reducing the blower speed over a period of time but increasing the blower speed in incremental steps each time a snore is detected by the microphone 11.

In use, a patient may connect himself to the CPAP unit and go to sleep. The CPAP pressure is initially at a minimum operating value of, for example, approximately 3 cm $H_2O$ gauge pressure so as not to cause the previously mentioned operational problems of higher initial pressures. Not until some time after going to sleep, and the patient's body relaxes, will the airway start to become unstable and the patient start to snore. The detection apparatus 22 will then respond to a snore, or snore pattern, and via the processor 26 increase the motor speed such that CPAP pressure increases by 1 cm $H_2O$ for each snore detected. The CPAP pressure can be increased relatively rapidly, if the patient's condition so requires, to a working pressure of the order of 8–10 cm, which is a typical requirement. An upper pressure limiting device can be incorporated for safety. Also, for ease of monitoring the variation over time in patient conditions, a parameter such as pressure output can be recorded in some convenient retrievable form for periodic study by the physician.

If for example in the early stages of sleep some lesser CPAP pressure will suffice, the CPAP unit of the present invention will not increase the pressure until needed, that is, unless the airway becomes unstable and snoring recommences no increase is made to the airway pressure.

By continuously decreasing the CPAP pressure at a rate of, for example, 1 cm $H_2O$ each 15 mins. in the absence of snoring the pressure is never substantially greater than that required to prevent apnea. However, when a snore or snoring pattern is detected, the decreasing CPAP pressure mode will be completely overwhelmed by a greater increase, about 1 cm $H_2O$ per detected snore or snoring pattern. Once a stable sleeping pattern is achieved, the preferred embodiment will then continually test to ensure that the CPAP pressure is as low as is practicable. Should the CPAP pressure be decreased to such an extent that the upper airway becomes unstable and snoring recommences, the pressure is reincreased to ensure that apnea is prevented, it being remembered that the snoring pattern is a precursor to apneic episodes.

The flexibility of the invention can be illustrated by the following example.

It is known that a patient's maximum propensity to suffer sleep apnea occurs during REM sleep. An airway that was otherwise stable at a given CPAP pressure may become unstable during REM sleep. Should this happen snoring will set in before apnea occurs. In such circumstances, the present invention will raise the CPAP pressure in response to the snoring, thus preventing the onset of apnea. The REM sleep passes, the patient's airway becomes more stable and the higher airway pressure is no longer required. In such circumstances, the CPAP pressure will be gradually reduced until the first sign of snoring reoccurs at which point the pressure will again be increased.

A patient normally makes at least one loud snort or snoring sound at the end of an occurrence of apnea and the present invention will respond to this unusually loud sound to increase the CPAP pressure. Thus even if apnea should occur without the usual precursor of snoring, the airway pressure can still be adjusted upward in response to the abnormally loud breathing sounds generated at the end of the apneic period.

The present invention thus provides a CPAP device which modifies the CPAP pressure according to variations in a patient's requirements throughout an entire sleep period. It will be clear to those skilled in the art that the present invention can cope with the variation in airway pressure requirements such as may occur during a single sleep period, it will also be able to cope with variations in CPAP pressure requirements due to a general improvement or deterioration in a patient's general condition as may take place over a longer period of time.

Figure 4:
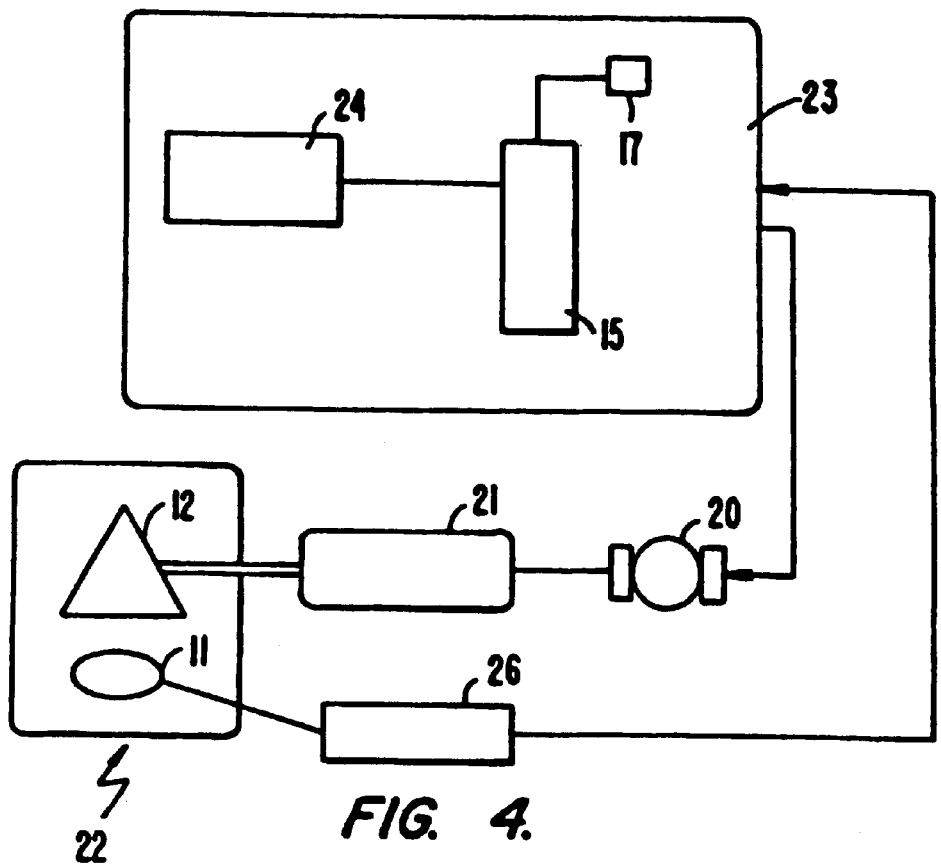
FIG. 4 is a circuit diagram of the device of FIG. 3.

FIG. 4 illustrates in block form the circuitry of the CPAP device of FIG. 3. A snoring detection apparatus 22 is comprised of the microphone 11 attached to the nose mask 12. The electrical signals of the microphone 11 are sent to a Filter/Amplifier/Processor 26 which generates a control signal indicative of the recognition of a snoring pattern equivalent to a predetermined pattern.

Such control signals are sent to a feedback speed controller 23. The speed controller 23 comprises a ramp generator and voltage to frequency converter 24 for control of a switch mode power supply (SMPS) 15, which provides the power to run the motor 20 turning the blower 21.

The maximum output of the SMPS 15, and therefore the maximum pressure delivered to the mask 12, is limited by a pressure time control 17.

Figure 6:
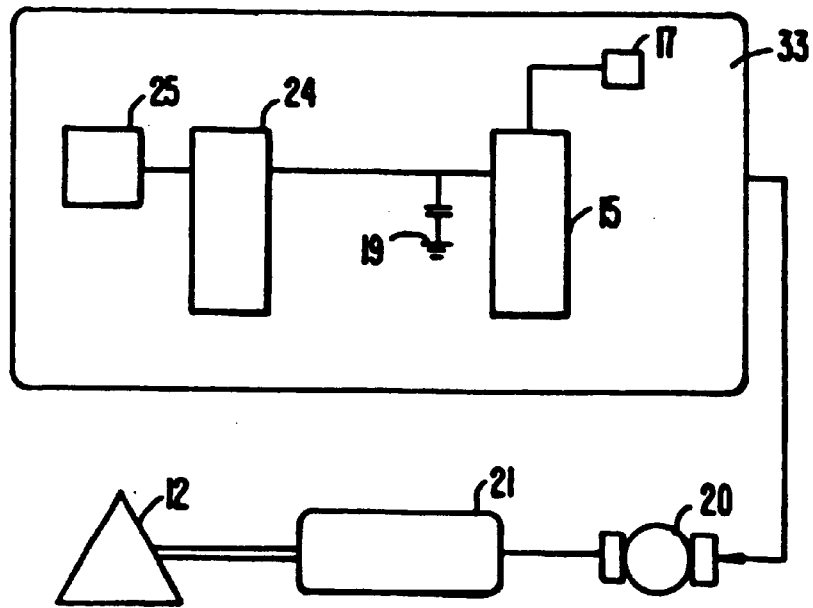
FIG. 6 is a circuit diagram of the device of FIG. 5.
Figure 5:
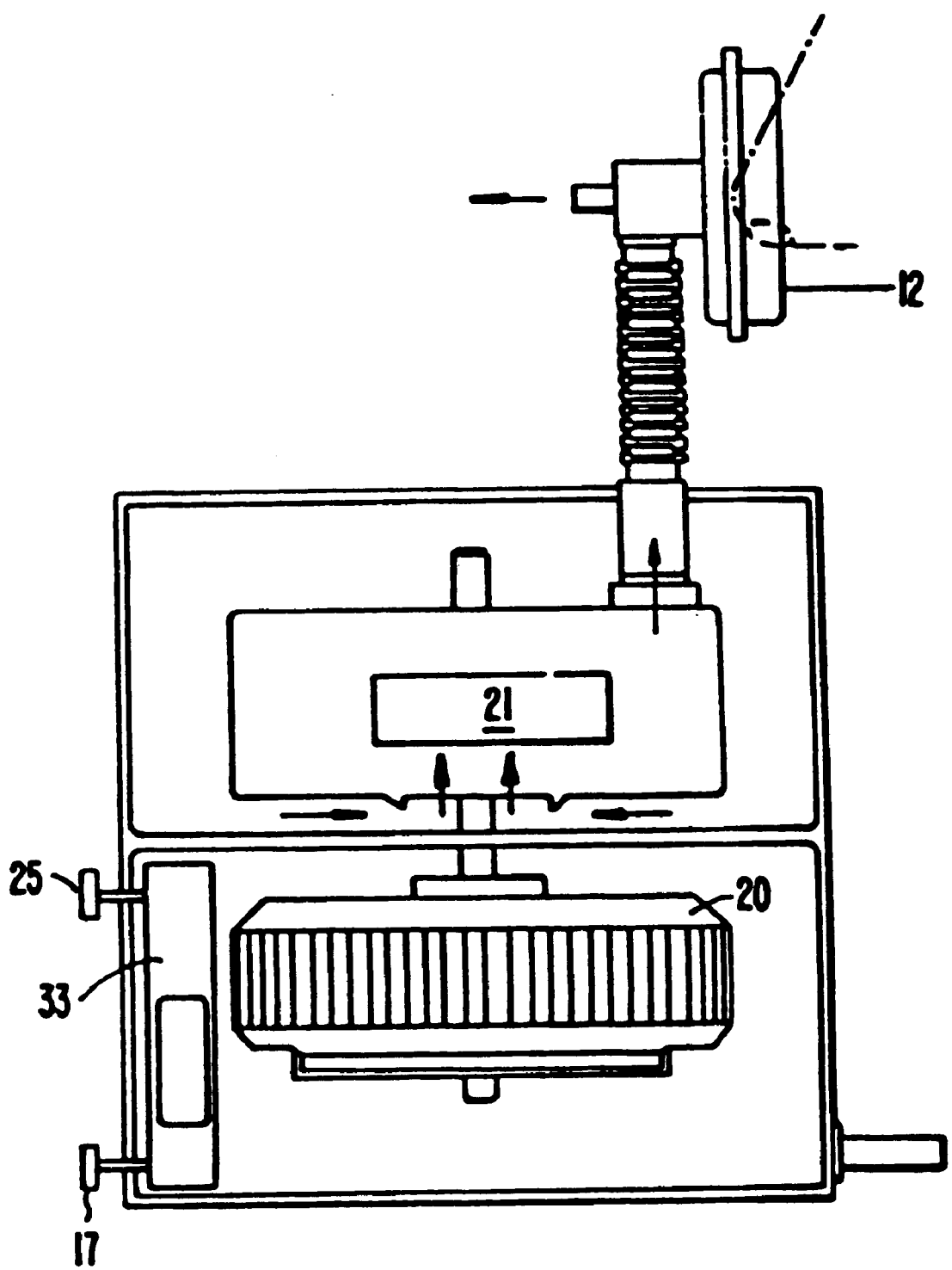
FIG. 5 is a diagram of an embodiment of another aspect of the invention.

In another aspect of the invention, shown in FIGS. 5 and 6, there is provided a control circuit 33 comprising a delay control 25, a timer 24, a switch mode power supply (SMPS) 15, and an upper pressure control 17. In the timer 24 a square wave pulse train, is generated where the duty ratio can be varied by the delay control 25. This pulse train, in the form of a current, is applied to a capacitor 19 to obtain a ramp voltage. Hence the output of the timer 24 and the input of the SMPS 15 is a voltage increasing with respect to time. The output of the SMPS 15, and therefore the motor voltage and speed, follow the input.

The minimum blower speed is preset so as to give effective operation of the air blower 21 and a minimum airway pressure which is comfortable to the patient. Typically a minimum pressure of 3–5 cm $H_2O$ will have negligible effect on most patients.

The desired maximum airway pressure, being the intended therapeutic airway pressure, is set by adjusting the variable control 17. The magnitude of this pressure will vary according to the requirements of the individual patient but will typically be in the range 10–20 cm $H_2O$.

When the delay control 25 is not set to zero minutes, the apparatus commences operation at the minimum motor speed and gradually increases the motor speed over a period of time selected before reaching the maximum preselected speed according to the previous adjustment of control 17. When the delay control 25 is set to zero minutes airway pressure comes up to the full level as set by adjustment 17 in a short period of time.

By this arrangement sleep is commenced with a low and comfortable air pressure but then automatically increased after a selectable period of time to the desired therapeutic pressures so as to provide an adequate pneumatic splint to the airway passages during the latter stages of sleep when apnea is likely.

A convenient way to gauge whether a correct therapeutic, or maximum, pressure has been selected is to use the diagnostic device 10 of this invention while the patient is undergoing CPAP therapy. Should the recorded data show no signs of apneic periods then the setting may be assumed to be adequate at least for the patient when in a similar physical condition. Another long term benefit can, be gained by recording the pressure level applied to the patient during sleep periods in which CPAP is applied using the feedback device of this invention. By making such recordings spaced over a period of time the skilled physician can diagnose any long term changes in the patient's condition.

Figure 7:
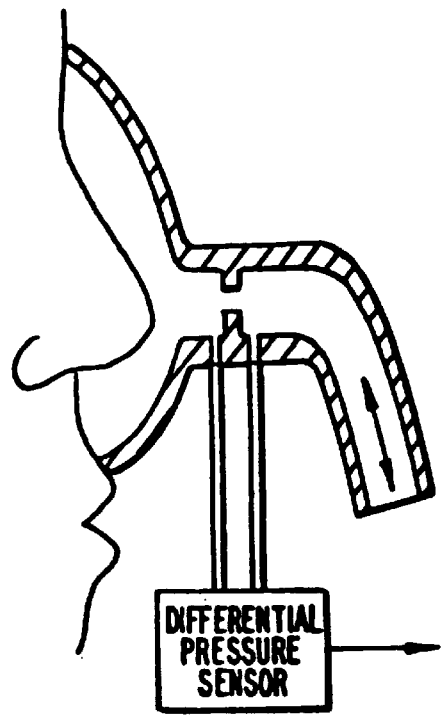
FIG. 7 is a schematic sectional view of one embodiment of a more general apparatus for detecting snoring and/or other respiratory parameters in accordance with the present invention.

FIG. 7 illustrates a pressure detection device comprising a pressure sensor, in pressure communication with the container of a nose mask. Air, being inhaled by the patient, enters the nasal passageways through the opening in the nose mask and is exhaled in the reverse direction. The pressure sensor is ideally located to detect both pressure waves generated by the patient snoring or by variations in the respiration rate or pattern of the patient. Hence the snoring sounds and breathing variations are captured and concentrated by this arrangement. Alternatively, the pressure sensor may be located within or attached externally to a nasal prong device.

Figure 12:
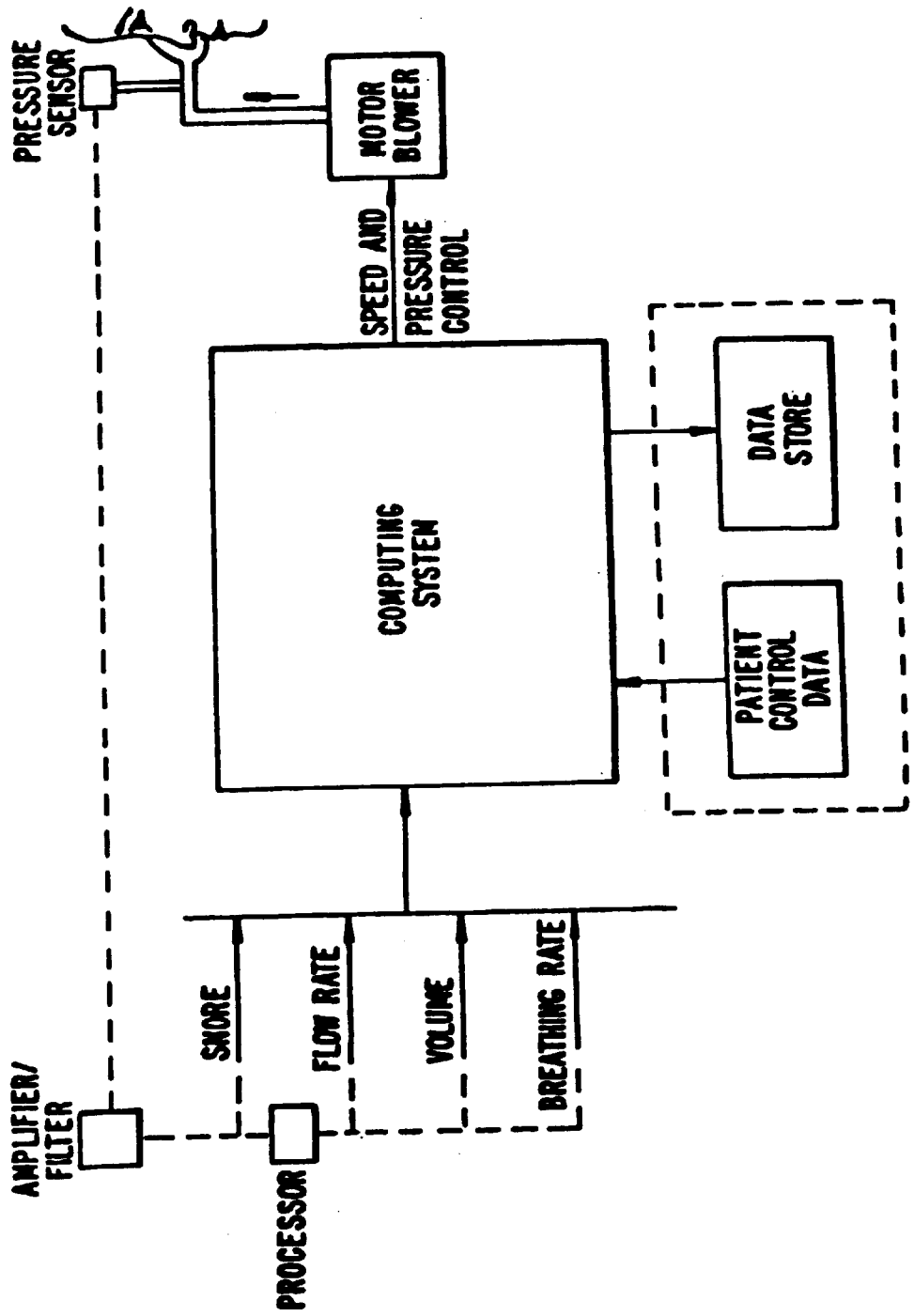
FIG. 12 shows in schematic form how the computing system which analyzes the parameters of interest with reference to control patient data controls motor speed and air pressure delivered to the patient; and, FIG. 13 shows an example of how the pressure wave generated by snoring progressively increases/decreases the air pressure delivered to the patient as directed by the computing system.

The detection device can be used in a diagnostic device or a feedback control. In the case of the detection device being used in diagnostic equipment there is connected to the pressure sensor a computing system as shown in FIG. 12 which analyses and records signals from the pressure sensor in a data store. These signals can be stored on a real time basis or after further processing in the form of indexes such as the number of apneic episodes, the number of hypopneas, their duration, etc. The recorded data can then be reviewed by a physician for diagnosis.

Figure 9:
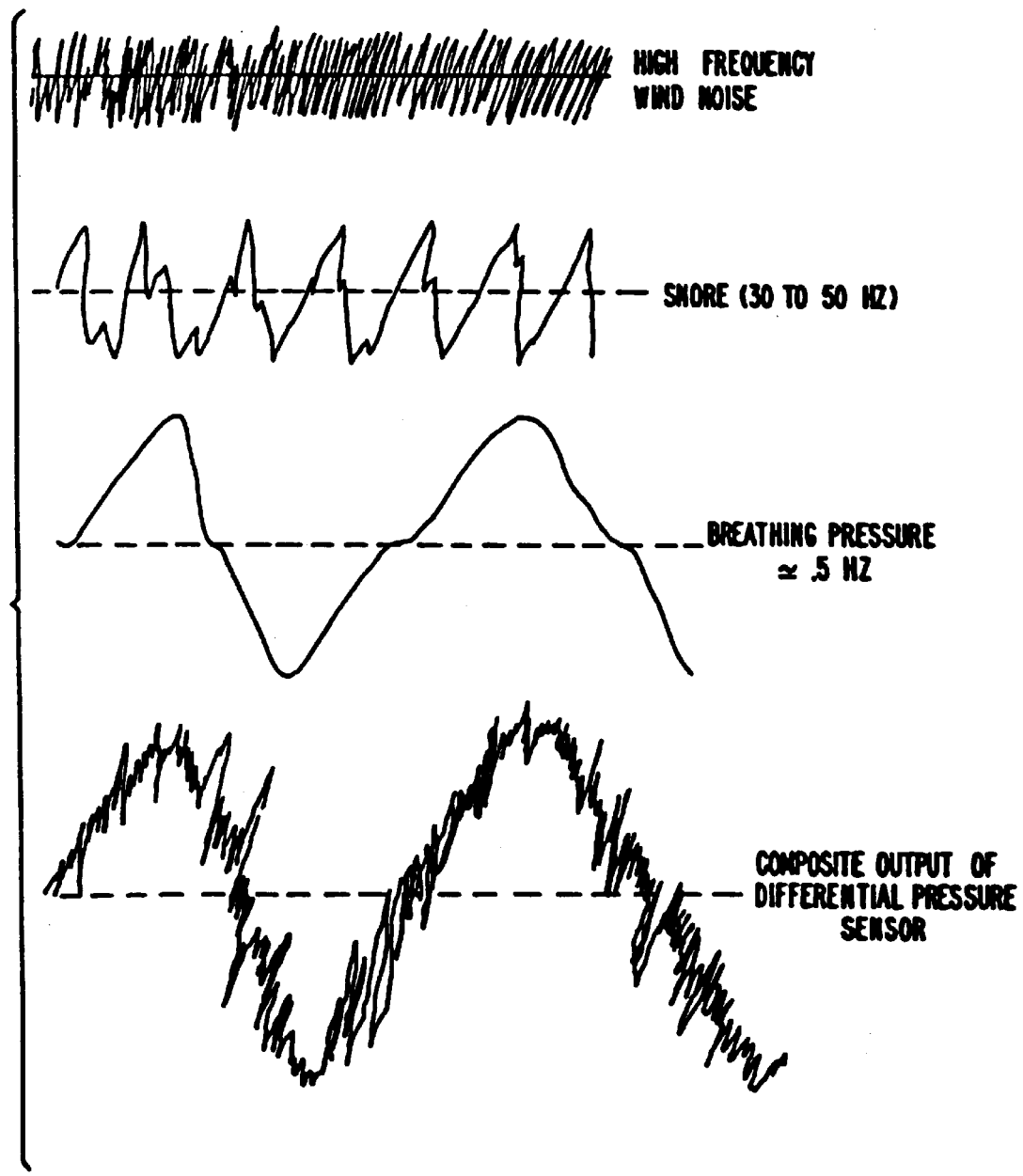
FIG. 9 shows the different pressure waves generated by the extraneous high frequency noise associated with air flow from the blower and the pressure waves of interest indicative of snoring and breathing and the composite wave comprising the contribution of all sources of pressure wave.

FIG. 9 shows the sources of pressure waves detected by the pressure sensor. The high frequency wind noise is generated by the air blower and is extraneous for the purposes of interpreting the condition of the patient. Pressure waves at a frequency of 30 to 50 Hz are indicative of snoring and could be detected by using a particular embodiment of the pressure sensor in the form of a microphone. Disturbances in breathing pattern are detected at a very low frequency relating to breathing rate of approximately 0.5 Hz. The output of the sensor is a composite of the pressure waves generated by all these sources.

Figure 10:
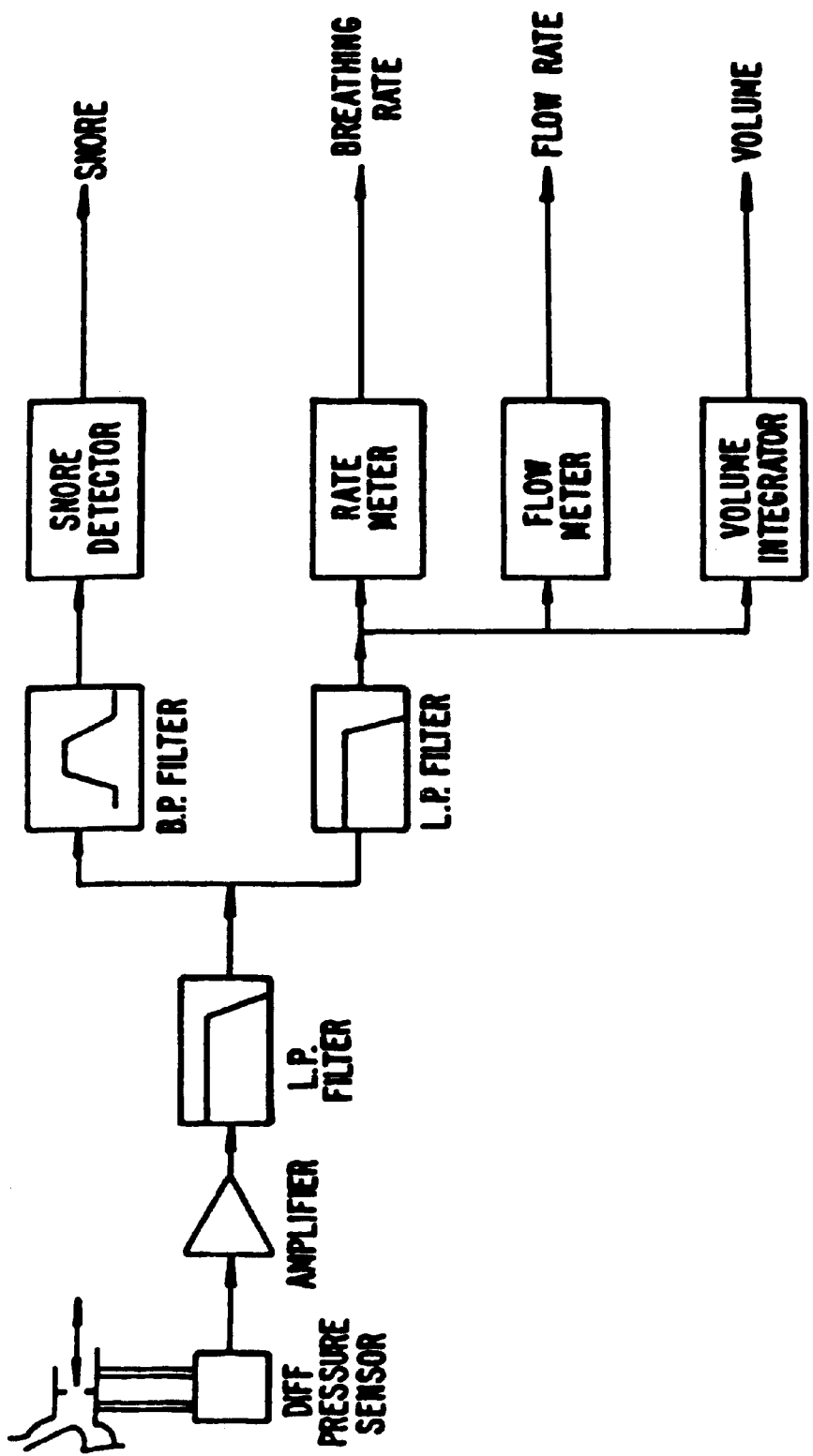
FIG. 10 shows how the composite wave from the pressure sensor is filtered to generate information on the parameters of interest.

FIG. 10 Shows a schematic electronic circuit which first amplifies the output of the pressure sensor before passing it through a series of filters to separate the pressure waves at the frequencies of interest. The high frequency wind noise is eliminated and signals indicative of snoring and breathing are obtained. The breathing signal is further processed to give information on breathing rate, flow rate and volume per breath.

FIG. 2a shows a graph representing sound amplitudes obtained from the snoring signal filtered from the pressure detection device. The major calibration in the time scale direction represents two minutes.

The effect of blower motor noise can be diminished or completely removed by setting a low gain on the recording device or passing the signal through an amplitude filter to effectively ignore all sounds below a particular minimum amplitude or by passing the signals through a low pass frequency filter to effectively ignore sounds above its cut-off frequency. An alternative method is to use a sound attenuator in the air line proximate the blower.

Part A of FIG. 2a is indicative of normal breathing, part B indicates soft to moderate snoring, part C shows constant loud snoring and part E shows periods of silence punctuated by snoring. In section D of the chart of FIG. 2a, it can be seen that the breathing sound intensity rises and falls. This is indicative of obstructive hypopnea, a condition in which the breath-by-breath intensity decreases progressively, and then increases. In this pattern the decreasing intensity of the snoring occurs when the upper airway is almost, but not entirely, sucked closed by strong inspiratory efforts. This pattern is a "pre-apneic" pattern.

The following part E is therefore quickly interpreted by a skilled physician as being indicative of sleep apnea, with periods of airway occlusion which terminate with one or more loud breathing sounds followed by further occlusions.

The correlation between snoring patterns and arterial oxygen is shown in FIG. 2b. Clearly the snoring patterns are an accurate parameter for detecting imminent apneic episodes, and more importantly periods of low oxygen supply to the brain and other organs.

Figure 8:
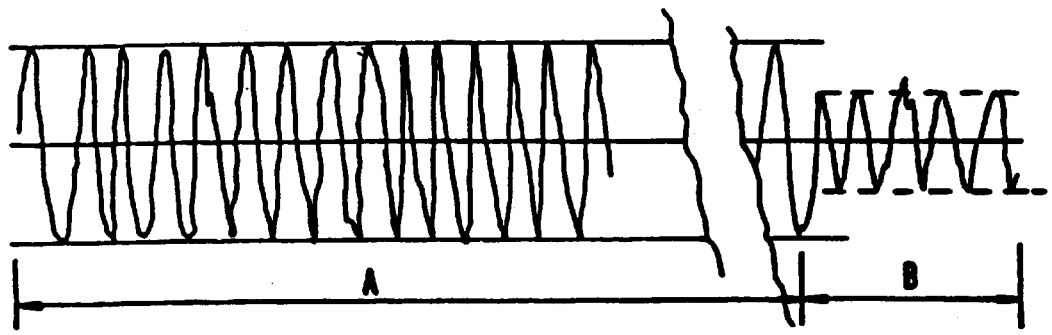
FIG. 8 shows the volume of air breathed by a patient in normal sleep contrasted with the declining volume breathed as the patient starts to hypoventilate.

FIG. 8 shows the volume of air inhaled (or exhaled) by the patient with each breath as determined by the volume integrator from the breathing signal filtered from the pressure sensor. Part A of FIG. 8 shows normal breathing, while Part B shows shallow breathing or hypoventilation. A decreasing pattern of air volume inspired by the patient can be indicative of the imminent onset of apnea or can be undesirable as the patient's arterial oxygen level falls below an acceptable level.

FIG. 10 shows how the processing system can be set up to respond when the average volume of a predefined number of the most recent breaths falls below the volume of a predefined long term average volume for that patient.

Figure 11:
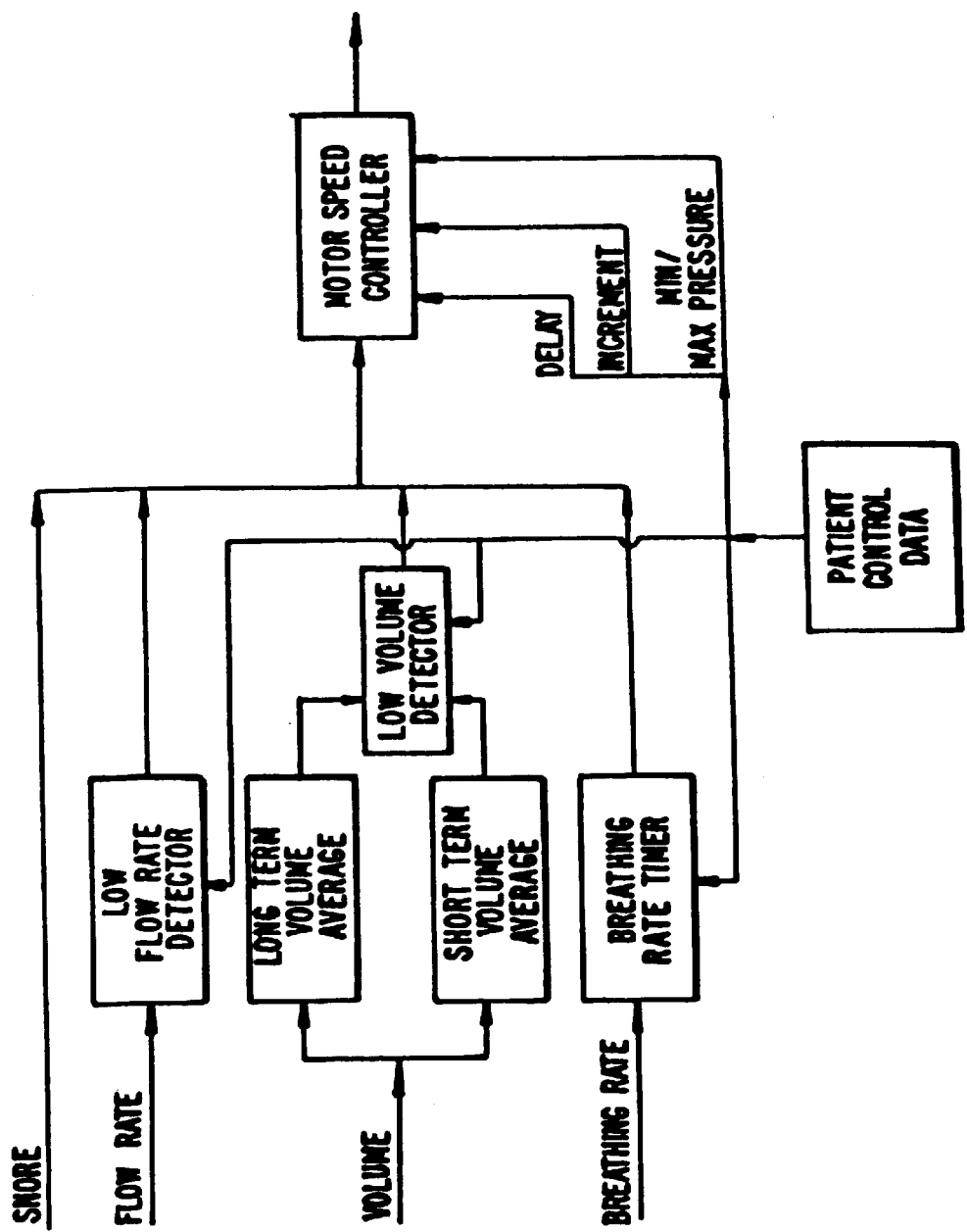
FIG. 11 shows in schematic form how any or all of these parameters can be used either alone or by reference to control data to provide a signal to a Motor Speed Controller.

FIG. 11 shows how the computing system can accept and analyze any or all of the processed signals from the pressure sensor and using the signal, alone or by comparison with control data for that patient, control the speed of the blower to vary the pressure of the air delivered to the patient's nose mask.

Figure 13:
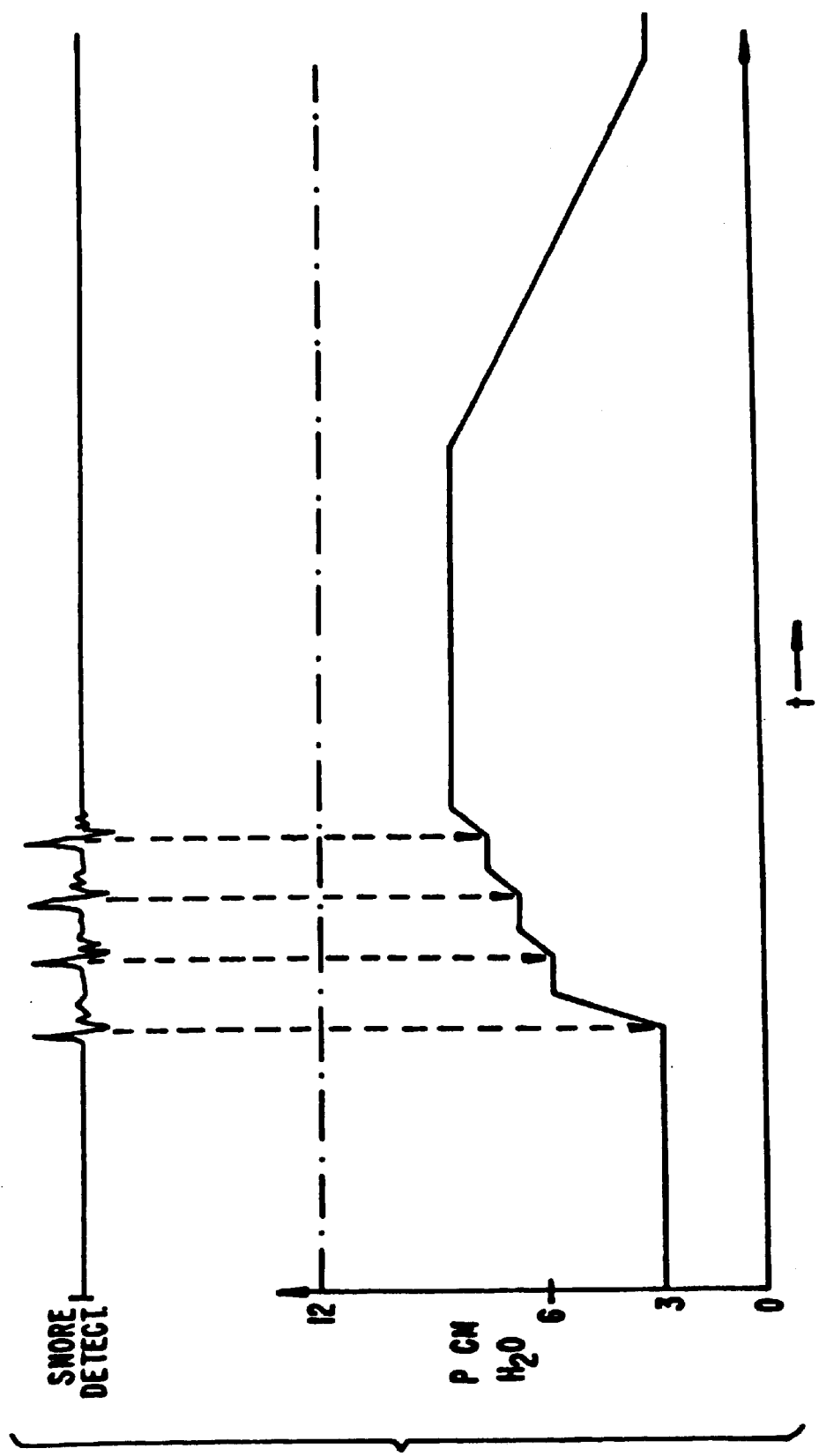

FIG. 13 shows an example of how the signal indicative of snoring alone is received by the computing system and the computing system increases pressure in accordance with predefined procedure.

Thus, the recorded information derived from the signal of the pressure sensor can be used for diagnostic purposes, such as initial diagnosis of sleep apnea or hypopnea, without the need for the patient to stay overnight in an observation facility, the sound and breathing patterns can be analyzed by a programmed microprocessor or computing system as shown in FIG. 12 so as to record tables of indexes such as number of hypopneas and/or apneic episodes, their duration and time of occurrence. This is of economic significance because the cost of one overnight observation is comparable to the purchase price of a CPAP device.

Furthermore, diagnostic apparatus in accordance with the present invention is suited for use by a patient with minimal supervision and therefore may be used successfully at home, the recorded diagnostic information being conveniently presented for expert analysis.

In FIG. 3, a CPAP apparatus embodying the invention is illustrated. The CPAP unit comprises a motor 20 which drives a blower 21. The speed of the motor 20 is controlled by an electronic speed control unit 23. As an increase in motor speed also increases blower speed which in turn increases the output air pressure of blower 21, the speed control unit can be manipulated to vary the output pressure of the blower 21. The CPAP device also includes a pressure detection means 22 wherein pressure waves in the form of electrical signals are detected by a pressure sensor 11. The pressure detection means 22 is conveniently in the form of the previously described device illustrated in FIG. 7. Electrical signals are fed from said sensor 11 to an amplifier/filter/processor unit 26 which may be inside or outside the blower unit casing and generates an electrical signal when snoring sounds and/or deviations of breathing parameters from predetermined values occur. The motor speed control means is electrically connected to the pressure detection device 22 while being electrically isolated from the patient and increases the speed of the electric motor 20 by an analogue means in response to the electrical signal generated by the pressure detection device. Accordingly, the output pressure of the CPAP unit increases in response to detection of snoring and/or deviations of breathing parameters from predetermined values.

The method of operation can be illustrated by considering the effect of a snore or sequence of snores detected by the pressure sensor as shown in FIG. 13. When a snore or sequence of snores is detected by the snoring detection means 22 a signal is generated. The speed control unit 23 increases the speed of the fan motor and the output pressure is increased. As snoring is caused by vibration of the soft palate, it is therefore indicative of an unstable airway and, as previously described, is a warning signal of the imminence of upper airway occlusion in patients that suffer obstructive sleep apnea. Snoring is itself undesirable not only as it is a disturbance to others but it is strongly believed to be connected with hypertension. If the resultant increase in CPAP pressure is sufficient to completely stabilize the airway, snoring will cease. If a further snoring sound is detected, the CPAP pressure is increased again. This process is repeated until the upper airway is stabilized and snoring ceases. Hence, the occurrence of obstructive apnea can be eliminated by application of a minimum appropriate pressure at the time of use.

In order to ensure that the CPAP pressure is maintained at a level as low as practicable to prevent the onset of apnea, the preferred embodiment also includes a means to decrease the pressure if an extended period of snore free breathing occurs. For example, this can be done by automatically reducing the CPAP pressure at a gradual rate as long as snoring is not detected. The rate at which the CPAP pressure is decreased in the absence of snoring is preferable much less than the rate at which it is increased when snoring is detected. This can be achieved, for example, by the amplifier/filler/processor unit 26, the absence of an electronic signal from the pressure sensor 11, continuously gradually reducing the blower speed over a period of time but increasing the blower speed in incremental steps each time a snore is detected by the pressure sensor 11.

A predetermined deviation of any or all of the breathing parameters, flow rate, volume or breathing rate from a predetermined common value can generate a signal in a similar way. Hence a fall in the volume of air inspired or expired per breath below a preset value can generate a signal which increases the speed of the fan motor and increases the output pressure. After the breathing volume has returned to the control setting for a predetermined period, the fan motor speed will be decreased slowly until a snore or unacceptable breathing pattern is again detected by the pressure sensor.

In use a patient may connect himself to the CPAP unit and go to sleep. only one connection is required apart from the normal CPAP circuit and this is simply the connection from the pressure sensor to the amplifier/filter/processor unit. No electrodes or other sensors have to be attached to the patient's body as the pressure sensor is conveniently located in the CPAP mask. The CPAP pressure is initially at a minimum comfortable operating value of, for example, approximately 3 cm $H_2O$ gauge pressure so the as not to cause the previously mentioned operational problems of higher initial pressures. Not until some time after going to sleep, and the patient's body relaxes, will the airway start to become unstable and the patient start to snore or exhibit abnormal breathing patterns. The detection apparatus 22 will a respond to the snore, or snore pattern or abnormal breathing pattern and via the processor 26 increase the motor speed such that CPAP pressure increases by 1 cm $H_2O$ for each snore or predetermined abnormality in breathing pattern detected. The CPAP pressure can be increased relatively rapidly, if the patient's condition so requires, to a working pressure of the order of 8–10 cm $H_2O$, which is a typical requirement. An upper pressure limiting device can be incorporated for safety. Also, for ease of monitoring the variation over time in patient conditions, a parameter such as pressure output can be recorded in some convenient retrievable form for periodic study by the physician.

If for example in the early stages of sleep some lesser CPAP pressure will suffice, the CPAP unit of the present invention will not increase the pressure until needed, that is, unless the airway becomes unstable and snoring or abnormal breathing patterns recommence, no increase is made to the airway pressure.

By continuously decreasing the CPAP pressure as a rule of, for example, 1 cm $H_2O$ each 15 mins in the absence of snoring or abnormal breathing patterns, the pressure is never substantially greater than that required to prevent apnea or other undesirable respiratory conditions. However, when a snore, or snoring patterns or abnormal breathing pattern, is detected the decreasing CPAP pressure mode will be completely overwhelmed by a greater increase, about 1 cm $H_2O$ per predetected snore or snoring pattern or predetermined abnormality in breathing pattern. Once a stable sleeping pattern is achieved, the preferred embodiment will a continually test to ensure that the CPAP pressure is as low as is practicable. Should the CPAP pressure be decreased to such an extent that the upper airway becomes unstable and snoring or unacceptable breathing patterns recommence, the pressure is reincreased to ensure that apnea is prevented, it being remembered that the snoring or abnormal breathing pattern is a precursor to apneic episodes or other undesirable respiratory conditions such as shallow breathing or hypopnea.

The flexibility of the invention can be illustrated by the following example.

It is known that a patient's maximum propensity to suffer sleep apnea occurs during REM sleep. An airway that was otherwise stable at a given CPAP pressure may become unstable during REM sleep. Should this happen snoring and/or particular deviations in breathing patterns will set in before apnea occurs. In such circumstances, the present invention will raise the CPAP pressure in response to the snoring or deviation in breathing patterns, thus preventing the onset of apnea or other undesirable respiratory condition. After the REM sleep passes, the patient's airway becomes more stable and the higher airway pressure is no longer required. In such circumstances, the CPAP pressure will be gradually reduced until the first sign of snoring and/or unacceptable breathing patterns reoccurs at which point the pressure will again be increased.

A patient normally makes at least one loud snort or snoring sound at the and of an occurrence of apnea and the present invention will respond to this unusually loud sound to increase the CPAP pressure. Thus even if apnea should occur without the usual precursor of snoring or abnormal breathing pattern, the airway pressure can still be adjusted upward in response to the abnormally loud breathing sounds generated at the end of the apneic period.

The present invention thus provides a CPAP device which modifies the CPAP pressure according to variations in a patient's requirements throughout an entire sleep period. It will be clear to those skilled in the art that the present invention can cope with the variation in airway pressure requirements such as may occur during a single sleep period, it will also be able to cope with variations in CPAP pressure requirements due to a general improvement or deterioration in a patient's general condition as may take place over a longer period of time.

FIG. 12 illustrates in block form the circuitry of the feedback system. A pressure detection apparatus is provided either integral with or attached to the CPAP mask worn by the patient. The electrical signals from the pressure transducer are amplified and filtered to provide pressure waves of the desired frequencies indicative of snoring and breathing. The pressure wave indicative of breathing is further processed to generate signals indicative of flow rate, volume and breathing rate. Any or all signals are fed to a computing system which analyses the signals for deviation from predetermined values or patterns. The computing system may itself calculate control values of patterns for each patient based on moving average values or such values or patterns will be pre-programmed into the computing system.

Where signals deviate from predetermined values or patterns the computer system generates a signal which is sent to the feedback speed controller on the blower motor. Increasing blower speed increases the air pressure and level of CPAP treatment delivered to the patient. The speed and pressure are increased until signals detected from the patient are within the acceptable range of control values or patterns and the speed and pressure are maintained at that level.

The maximum output of the blower can be limited by limiting the signal from the computer to correspond to a predetermined motor speed.

A convenient way to gauge whether a correct therapeutic or maximum, pressure has been selected is to use the diagnostic device shown in FIG. 7 of this invention while the patient is undergoing CPAP therapy. Should the recorded data show no signs of apneic periods then the setting may be assumed to be adequate at least for the patient when in a similar physical condition. Another long term benefit can be gained by recording the pressure level applied to the patient during sleep periods in which CPAP is applied using the feedback device of this invention. By making such recordings spaced over a period of time the skilled physician can diagnose any long term changes in the patient's condition.

It is to be understood that while the invention has been described above in conjunction with preferred specific embodiments, the description and examples are intended to illustrate and not limit the scope of the invention, which is defined by the scope of the appended claims.

What is claimed is:

1. A method of diagnosing whether a patient has obstructive sleep apnea, comprising:
    providing the patient with an apnea monitoring apparatus configured for home use to monitor the patient's snoring and flow rate, the apnea monitoring apparatus being in communication with a nasal mask configured to be worn over the patient's nasal passages;
    allowing the patient to sleep at home while being monitored by the apnea monitoring apparatus;
    generating data indicative of the monitored snoring and flow rate during the patient's home sleep;
    analyzing the snoring and flow rate data; and
    diagnosing the presence of obstructive sleep apnea based at least in part on the snoring and flow rate data.

2. A method according to claim 1, further comprising recording and storing the signal over a period of time.

3. A method according to claim 1, further comprising:
    providing a predetermined snoring and flow rate pattern;
    comparing the patient's snoring and flow rate with the predetermined snoring and flow rate pattern; and
    controlling pressure within the nasal mask based on the comparison between the patient's snoring and flow rate and the predetermined snoring and flow rate pattern.

4. A method according to claim 1, further comprising:
    connecting a pressure sensor in communication with the nasal mask, the pressure sensor being configured to provide a signal indicative of the patient's snoring and flow rate; and
    processing the signal to assist in the diagnosis of obstructive sleep apnea.

5. A method according to claim 4, further comprising connecting the pressure sensor to the nasal mask adjacent an air inlet of the nasal mask to provide the signal.

6. A method according to claim 4, further comprising connecting the pressure sensor remote from the nasal mask so as to be in pressure communication with the patient's respiratory system to provide the signal.

7. A method according to claim 1, wherein the diagnosing comprises providing the signal to a sleep disorder clinical professional.

8. A method according to claim 1, wherein the analyzing comprises processing the snoring and flow rate data to provide at least one index useful in the diagnosis of obstructive sleep apnea.

9. A method according to claim 8, wherein the diagnosing comprises reviewing the index to screen the patient for an indication of obstructive sleep apnea.

10. A method according to claim 1, further comprising monitoring a non-respiratory parameter.

11. A method according to claim 10, wherein the non-respiratory parameter includes one of pulse oximetry and ECG.

12. A method according to claim 10, wherein the non-respiratory parameter is a non-EKG parameter.

13. A method of diagnosing a patient for the condition of obstructive sleep apnea, the method comprising:
    monitoring the patient's snoring and flow rate at home in a non-clinical environment for at least one night, the monitoring being accomplished by a monitoring apparatus, the monitoring apparatus being in communication with a nasal mask;
    generating data indicative of the patient's snoring and flow rate at home; and
    diagnosing the presence of obstructive sleep apnea based at least in part on the data.

14. A method according to claim 13, further comprising recording and storing the signal over a period of time.

15. A method according to claim 13, further comprising:
    providing a predetermined snoring and flow rate pattern;
    comparing the patient's snoring and flow rate with the predetermined snoring and flow rate pattern; and
    controlling pressure within the nasal mask based on the comparison between the patient's snoring and flow rate and the predetermined snoring and flow rate pattern.

16. A method according to claim 13, further comprising:
    connecting a pressure sensor in communication with the nasal mask, the pressure sensor being configured to provide a signal indicative of the patient's snoring and flow rate; and
    processing the signal to assist in the diagnosis of obstructive sleep apnea.

17. A method according to claim 16, further comprising connecting the pressure sensor to the nasal mask adjacent an air inlet of the nasal mask to provide the signal.

18. A method according to claim 16, further comprising connecting the pressure sensor remote from the nasal mask so as to be in pressure communication with the patient's respiratory system to provide the signal.

19. A method according to claim 13, wherein the diagnosing comprises providing the signal to a sleep disorder clinical professional.

20. A method according to claim 13, wherein the generating comprises processing the snoring and flow rate data to provide at least one index useful in the diagnosis of obstructive sleep apnea.

21. A method according to claim 20, wherein the diagnosing comprises reviewing the index to screen the patient for an indication of obstructive sleep apnea.

22. A method according to claim 13, further comprising monitoring a non-respiratory parameter.

23. A method according to claim 22, wherein the non-respiratory parameter includes one of pulse oximetry and ECG.

24. A method according to claim 22, wherein the non-respiratory parameter is a non-EKG parameter.

25. A method of diagnosing a patient for the condition of obstructive sleep apnea, comprising:
    providing the patient with an apparatus configured for home monitoring of the frequency and severity of a patient's snoring, flow rate, hypopnea and apnea, the apparatus being in communication with a nasal mask;
    generating data at the patient's home indicative of the frequency and severity of the patient's snoring, hypopnea and apnea; and
    diagnosing the presence of obstructive sleep apnea on the basis of the data.

26. A method according to claim 25, further comprising recording and storing the signal over a period of time.

27. A method according to claim 25, further comprising:
    providing a predetermined snoring and flow rate pattern;
    comparing the patient's snoring and flow rate with the predetermined snoring and flow rate pattern; and controlling pressure within the nasal mask based on the comparison between the patient's snoring and flow rate and the predetermined snoring and flow rate pattern.

28. A method according to claim 25, further comprising:
connecting a pressure sensor in communication with the nasal mask, the pressure sensor being configured to provide a signal indicative of the patient's snoring and flow rate; and
processing the signal to assist in the diagnosis of obstructive sleep apnea.

29. A method according to claim 28, further comprising connecting the pressure sensor to the nasal mask adjacent an air inlet of the nasal mask to provide the signal.

30. A method according to claim 28, further comprising connecting the pressure sensor remote from the nasal mask so as to be in pressure communication with the patient's respiratory system to provide the signal.

31. A method according to claim 25, wherein the diagnosing comprises providing the signal to a sleep disorder clinical professional.

32. A method according to claim 25, wherein the generating comprises processing the snoring and flow rate data to provide at least one index useful in the diagnosis of obstructive sleep apnea.

33. A method according to claim 32, wherein the diagnosing comprises reviewing the index to screen the patient for an indication of obstructive sleep apnea.

34. A method according to claim 25, further comprising monitoring a non-respiratory parameter.

35. A method according to claim 34, wherein the non-respiratory parameter includes one of pulse oximetry and ECG.

36. A method according to claim 34, wherein the non-respiratory parameter is a non-EKG parameter.

37. A method for determining whether a patient requires diagnosis of obstructive sleep apnea in a sleep clinic by home monitoring, the method comprising:
providing the patient with an apparatus configured for home monitoring of data indicative of the frequency and severity of the patient's snoring, flow rate, hypopnea and apnea, the apparatus being in communication with a nasal mask;
analyzing the data for the presence of snoring, hypopnea and apnea patterns which are indicative of a diagnosis of obstructive sleep apnea; and
referring the patient demonstrating the snoring, hypopnea and apnea patterns indicative of a diagnosis of obstructive sleep apnea during the home monitoring to a clinic environment for further clinical observation and testing.

38. A method according to claim 37, further comprising recording and storing the signal over a period of time.

39. A method according to claim 37, further comprising:
providing a predetermined snoring and flow rate pattern;
comparing the patient's snoring and flow rate with the predetermined snoring and flow rate pattern; and
controlling pressure within the nasal mask based on the comparison between the patient's snoring and flow rate and the predetermined snoring and flow rate pattern.

40. A method according to claim 37, further comprising:
connecting a pressure sensor in communication with the nasal mask, the pressure sensor being configured to provide a signal indicative of the patient's snoring and flow rate; and
processing the signal to assist in the diagnosis of obstructive sleep apnea.

41. A method according to claim 40, further comprising connecting the pressure sensor to the nasal mask adjacent an air inlet of the nasal mask to provide the signal.

42. A method according to claim 40, further comprising connecting the pressure sensor remote from the nasal mask so as to be in pressure communication with the patient's respiratory system to provide the signal.

43. A method according to claim 37, wherein the diagnosing comprises providing the signal to a sleep disorder clinical professional.

44. A method according to claim 37, wherein the analyzing comprises processing the snoring and flow rate data to provide at least one index useful in the diagnosis of obstructive sleep apnea.

45. A method according to claim 44, wherein the diagnosing comprises reviewing the index to screen the patient for an indication of obstructive sleep apnea.

46. A method according to claim 37, further comprising monitoring a non-respiratory parameter.

47. A method according to claim 46, wherein the non-respiratory parameter includes one of pulse oximetry and ECG.

48. A method according to claim 46, wherein the non-respiratory parameter is a non-EKG parameter.

49. A method of monitoring snoring and flow rate of a patient, the snoring and flow rate being useful in the diagnosis of obstructive sleep apnea, the method comprising:
providing a nasal mask to substantially surround the patient's nasal passages;
providing the nasal mask with access to a source of breathable gas and to the patient;
providing a sensor in communication with the nasal mask;
measuring snoring and flow rate of the patient with the sensor to generate a signal indicative of a value of the measured snoring and flow rate; and
processing the signal to assist in the diagnosis of obstructive sleep apnea.

50. A method according to claim 49, further comprising recording and storing the signal over a period of time.

51. A method according to claim 49, further comprising:
providing a predetermined snoring and flow rate pattern;
comparing the patient's snoring and flow rate with the predetermined snoring and flow rate pattern; and
controlling pressure within the nasal mask based on the comparison between the patient's snoring and flow rate and the predetermined snoring and flow rate pattern.

52. A method according to claim 49, further comprising connecting a pressure sensor to the nasal mask adjacent an air inlet of the nasal mask to provide the signal.

53. A method according to claim 49, wherein the sensing of the patient's snoring and flow rate is performed while the patient is sleeping substantially unsupervised in a non-clinical setting.

54. A method according to claim 49, further comprising connecting a pressure sensor remote from the nasal mask so as to be in pressure communication with the patient's respiratory system to provide the signal.

55. A method according to claim 49, further comprising providing the signal to a sleep disorder clinical professional in the diagnosis of obstructive sleep apnea.

56. A method according to claim 49, further comprising processing the signal to provide at least one index useful in the diagnosis of obstructive sleep apnea.

57. A method according to claim 56, further comprising reviewing the index to screen the patient for an indication of obstructive sleep apnea.

58. A method according to claim 49, further comprising monitoring a non-respiratory parameter.

59. A method according to claim 58, wherein the non-respiratory parameter includes one of pulse oximetry and ECG.

60. A method according to claim 58, wherein the non-respiratory parameter is a non-EKG parameter.

61. A method according to claim 49, wherein only the signal of the sensor is processed to assist in the diagnosis of obstructive sleep apnea.

62. A method useful in the diagnosis of obstructive sleep apnea of a patient, the method comprising:

providing a sensor connected to a nasal mask adjacent an air inlet of the nasal mask;

sensing the at least one respiratory parameter to provide a signal indicative of at least one respiratory parameter of the patient; and processing the signal to assist in the diagnosis of obstructive sleep apnea.

63. A method according to claim 62, further comprising connecting the sensor to the nasal mask in sound communication.

64. A method according to claim 63, wherein the at least one respiratory parameter is the patient's snoring or flow rate.

65. A method according to claim 63, further comprising:

providing a predetermined snoring and flow rate pattern;

comparing the patient's snoring and flow rate with the predetermined snoring and flow rate pattern; and controlling pressure within the nasal mask based on the comparison between the patient's snoring and flow rate and the predetermined snoring and flow rate pattern.

66. A method according to claim 63, further comprising recording and storing the signal over a period of time.

67. A method according to claim 62, wherein the sensing the at least one respiratory parameter is performed while the patient is sleeping substantially unsupervised in a non-clinical setting.

68. A method according to claim 62, further comprising connecting the sensor remote from the nasal mask so as to be in pressure communication with the patient's respiratory system, wherein the sensor is a pressure sensor.

69. A method according to claim 62, further comprising providing the signal to a sleep disorder clinical professional to assist in the diagnosis of obstructive sleep apnea.

70. A method according to claim 62, further comprising processing the signal to provide at least one index useful in the diagnosis of obstructive sleep apnea.

71. A method according to claim 70, further comprising reviewing the at least one index to screen the patient for an indication of obstructive sleep apnea.

72. A method according to claim 62, further comprising monitoring a non-respiratory parameter.

73. A method according to claim 72, wherein the non-respiratory parameter includes one of pulse oximetry, a non-EKG parameter and ECG.

74. A method of monitoring at least one respiratory parameter of a patient, the at least one respiratory parameter being useful in the diagnosis of obstructive sleep apnea, the method comprising:

providing a nasal mask to substantially surround the patient's nasal passages;

providing the nasal mask with access to a source of breathable gas and to the patient, connecting a sensor to the nasal mask adjacent an air inlet of the nasal mask to measure at least one respiratory parameter of the patient and transmit a signal indicative of a value of the measured at least one respiratory parameter; and processing the signal to assist in the diagnosis of obstructive sleep apnea.

75. A method according to claim 74, further comprising connecting the sensor to the nasal mask in sound communication.

76. A method according to claim 74, further comprising recording and storing the signal over a period of time.

77. A method according to claim 74, further comprising:

providing a predetermined at least one respiratory parameter;

comparing the at least one respiratory parameter with the predetermined at least one respiratory parameter; and controlling pressure within the nasal mask based on the comparison between the at least one respiratory parameter and the predetermined at least one respiratory parameter.

78. A method according to claim 74, wherein the at least one respiratory parameter is the patient's snoring or flow rate.

79. A method according to claim 74, wherein the measuring of the at least one respiratory parameter is performed while the patient is sleeping substantially unsupervised in a non-clinical setting.

80. A method according to claim 74, further comprising connecting the sensor remote from the nasal mask so as to be in pressure communication with the patient's respiratory system, wherein the sensor is a pressure sensor.

81. A method according to claim 74, further comprising providing the signal to a sleep disorder clinical professional to assist in the diagnosis of obstructive sleep apnea.

82. A method according to claim 74, further comprising processing the signal to provide at least one index useful in the diagnosis of obstructive sleep apnea.

83. A method according to claim 82, further comprising reviewing the index to screen the patient for an indication of obstructive sleep apnea.

84. method according to claim 74, further comprising monitoring a non-respiratory parameter.

85. A method according to claim 84, wherein the non-respiratory parameter includes one of pulse oximetry, a non-EKG parameter and ECG.

86. A method according to claim 74, wherein only the signal of the sensor is processed to assist in the diagnosis of obstructive sleep apnea.

87. A method of diagnosing whether a patient has obstructive sleep apnea, comprising:

providing the patient with an apnea monitoring apparatus configured for home use to monitor at least one respiratory parameter of the patient, the apnea monitoring apparatus being connected to a nasal mask adjacent an air inlet of the nasal mask, the nasal mask being configured to be worn over the patient's nasal passages;

allowing the patient to sleep at home while being monitored by the apnea monitoring apparatus;

generating data indicative of the monitored at least one respiratory parameter during the patient's home sleep;

analyzing the at least one respiratory parameter data; and diagnosing the presence of obstructive sleep apnea based at least in part on the at least one respiratory parameter data.

88. A method according to claim 87, further comprising recording and storing the signal over a period of time.

89. A method according to claim 87, further comprising:

providing a predetermined at least one respiratory parameter;

comparing the at least one respiratory parameter with the predetermined at least one respiratory parameter; and controlling pressure within the nasal mask based on the comparison between the at least one respiratory parameter and the predetermined snoring and flow rate pattern.

90. A method according to claim 87, wherein the at least one respiratory parameter is the patient's snoring or flow rate.

91. A method according to claim 87, further comprising:

connecting a pressure sensor to the nasal mask adjacent an air inlet of the nasal mask to provide a signal indicative of at least one respiratory parameter; and processing the signal to assist in the diagnosis of obstructive sleep apnea.

92. A method according to claim 91, further comprising connecting the pressure sensor to the nasal mask in sound communication.

93. A method according to claim 91, further comprising connecting the pressure sensor remote from the nasal mask so as to be in pressure communication with the patient's respiratory system.

94. A method according to claim 87, wherein the diagnosing comprises providing the signal to a sleep disorder clinical professional.

95. A method according to claim 87, wherein the analyzing comprises processing the at least one respiratory parameter to provide at least one index useful in the diagnosis of obstructive sleep apnea.

96. A method according to claim 95, wherein the diagnosing comprises reviewing the index to screen the patient for an indication of obstructive sleep apnea.

97. A method according to claim 87, further comprising monitoring a non-respiratory parameter.

98. A method according to claim 97, wherein the non-respiratory parameter includes one of pulse oximetry and ECG.

99. A method according to claim 97, wherein the non-respiratory parameter is a non-EKG parameter.

100. A method of diagnosing a patient for the condition of obstructive sleep apnea, the method comprising:

monitoring at least one respiratory parameter at home in a non-clinical environment for at least one night, the monitoring being accomplished by a monitoring apparatus, the monitoring apparatus connected to a nasal mask adjacent an air inlet of the nasal mask;

generating data indicative of at least one respiratory parameter at home; and diagnosing the presence of obstructive sleep apnea based at least in part on the data.

101. A method according to claim 100, further comprising connecting the monitoring apparatus to the nasal mask in sound communication.

102. A method according to claim 100, further comprising recording and storing a signal representative of at least one respiratory parameter data over a period of time.

103. A method according to claim 100, further comprising:

providing a predetermined at least one respiratory parameter;

comparing the at least one respiratory parameter with the predetermined at least one respiratory parameter; and controlling pressure within the nasal mask based on the comparison between the at least one respiratory parameter and the predetermined at least one respiratory parameter.

104. A method according to claim 100, wherein the at least one respiratory parameter is a patient's snoring or flow rate.

105. A method according to claim 100, further comprising connecting a pressure sensor to the nasal mask adjacent the air inlet of the nasal mask to provide a signal indicative of the patient's snoring and flow rate; and processing the signal to assist in the diagnosis of obstructive sleep apnea.

106. A method according to claim 105, further comprising connecting the pressure sensor remote from the nasal mask so as to be in pressure communication with the patient's respiratory system.

107. A method according to claim 100, wherein the diagnosing comprises providing the at least one respiratory parameter to a sleep disorder clinical professional.

108. A method according to claim 100, wherein the generating comprises processing the at least one respiratory parameter to provide at least one index useful in the diagnosing.

109. A method according to claim 108, wherein the diagnosing comprises reviewing the index to screen the patient for an indication of obstructive sleep apnea.

110. A method according to claim 100, further comprising monitoring a non-respiratory parameter.

111. A method according to claim 110, wherein the non-respiratory parameter includes one of pulse oximetry and ECG.

112. A method according to claim 110, wherein the non-respiratory parameter is a non-EKG parameter.

113. A method of diagnosing a patient for the condition of obstructive sleep apnea, comprising:

providing the patient with an apparatus configured for home monitoring of the frequency and severity of a patient's snoring, flow rate, hypopnea and apnea, the apparatus connected to a nasal mask adjacent an air inlet of the nasal mask;

generating data at the patient's home indicative of the frequency and severity of the patient's snoring, hypopnea and apnea; and diagnosing the presence of obstructive sleep apnea on the basis of the data.

114. A method according to claim 113, further comprising connecting the apparatus to the nasal mask in sound communication.

115. A method according to claim 113, further comprising recording and storing the signal over a period of time.

116. A method according to claim 113, further comprising:

providing a predetermined at least one respiratory parameter;

comparing the at least one respiratory parameter with the predetermined at least one respiratory parameter; and controlling pressure within the nasal mask based on the comparison between the at least one respiratory parameter and the predetermined at least one respiratory parameter.

117. A method according to claim 113, further comprising:

connecting a pressure sensor in communication with the nasal mask to provide a signal indicative of the at least one respiratory parameter; and processing the signal to assist in the diagnosis of obstructive sleep apnea.

118. A method according to claim 117, further comprising connecting the pressure sensor to the nasal mask adjacent an air inlet of the nasal mask to provide the signal.

119. A method according to claim 117, further comprising connecting the pressure sensor remote from the nasal mask so as to be in pressure communication with the patient's respiratory system.

120. A method according to claim 113, wherein the diagnosing comprises providing the at least one respiratory parameter to a sleep disorder clinical professional.

121. A method according to claim 113, wherein the generating comprises processing the at least one respiratory parameter to provide at least one index useful in the diagnosing.

122. A method according to claim 121, wherein the diagnosing comprises reviewing the index to screen the patient for an indication of obstructive sleep apnea.

123. A method according to claim 113, further comprising monitoring a non-respiratory parameter.

124. A method according to claim 123, wherein the non-respiratory parameter includes one of pulse oximetry and ECG.

125. A method according to claim 123, wherein the non-respiratory parameter is a non-EKG parameter.

126. A method for determining whether a patient requires diagnosis of obstructive sleep apnea in a sleep clinic by home monitoring, the method comprising:
    providing the patient with an apparatus configured for home monitoring of data indicative of the frequency and severity of the patient's snoring, flow rate, hypopnea and apnea, the apparatus connected to a nasal mask adjacent an air inlet of the nasal mask;
    analyzing the data for the presence of snoring, hypopnea and apnea patterns which are indicative of a diagnosis of obstructive sleep apnea; and
    referring the patient demonstrating the snoring, hypopnea and apnea patterns indicative of a diagnosis of obstructive sleep apnea during the home monitoring to a clinic environment for further clinical observation and testing.

127. A method according to claim 126, further comprising recording and storing the data over a period of time.

128. A method according to claim 126, further comprising:
    providing a predetermined data pattern;
    comparing the data with the predetermined data pattern; and
    controlling pressure within the nasal mask based on the comparison between the data and the predetermined data pattern.

129. A method according to claim 126, further comprising connecting the apparatus to the nasal mask in sound communication.

130. A method according to claim 126, further comprising:
    connecting a pressure sensor in communication with the nasal mask to provide a signal indicative of the at least one respiratory parameter; and
    processing the signal to assist in the diagnosis of obstructive sleep apnea.

131. A method according to claim 130, further comprising connecting the pressure sensor to the nasal mask adjacent an air inlet of the nasal mask to provide the signal.

132. A method according to claim 130, further comprising connecting the pressure sensor remote from the nasal mask so as to be in pressure communication with the patient's respiratory system.

133. A method according to claim 126, wherein the referring comprises providing the snoring and flow rate data to a sleep disorder clinical professional.

134. A method according to claim 126, wherein the analyzing comprises processing the snoring and flow rate data to provide at least one index useful in the diagnosis of obstructive sleep apnea.

135. A method according to claim 124, wherein the referring comprises reviewing the index to screen the patient for an indication of obstructive sleep apnea.

136. A method according to claim 130, further comprising monitoring a non-respiratory parameter.

137. A method according to claim 136, wherein the non-respiratory parameter includes one of pulse oximetry and ECG.

138. A method according to claim 136, wherein the non-respiratory parameter is a non-EKG parameter.

* * * * *

UNITED STATES PATENT AND TRADEMARK OFFICE
CERTIFICATE OF CORRECTION

PATENT NO.    : 6,635,021 B1
DATED         : October 21, 2003
INVENTOR(S)   : Sullivan et al.

It is certified that error appears in the above-identified patent and that said Letters Patent is hereby corrected as shown below:

Title page,
Item [30], Foreign Application Priority Data, change "June 26, 1997" to -- June 26, 1987 --;

Column 21,
Line 26, after word "claim", change "63" to -- 64 --;

Column 26,
Line 34, after word "claim", change "124" to -- 134 --.

Signed and Sealed this

Fourteenth Day of September, 2004

JON W. DUDAS
*Director of the United States Patent and Trademark Office*

UNITED STATES PATENT AND TRADEMARK OFFICE
CERTIFICATE OF CORRECTION

PATENT NO.    : 6,635,021 B1
DATED         : October 21, 2003
INVENTOR(S)   : Sullivan et al.

It is certified that error appears in the above-identified patent and that said Letters Patent is hereby corrected as shown below:

Title page,
Item [30], Foreign Application Priority Data, change "June 26, 1997" to -- June 26, 1987 --;

Column 21,
Line 26, after word "claim", change "63" to -- 64 --;

Column 26,
Line 34, after word "claim", change "124" to -- 134 --.

Signed and Sealed this

Fifth Day of October, 2004

JON W. DUDAS
*Director of the United States Patent and Trademark Office*